United States Patent
Zhang et al.

(10) Patent No.: US 10,544,155 B2
(45) Date of Patent: Jan. 28, 2020

(54) SPIROCYCLIC QUINOLIZINE DERIVATIVES USEFUL AS HIV INTEGRASE INHIBITORS

(71) Applicant: MERCK SHARP & DOHME CORP., Rahway, NJ (US)

(72) Inventors: Yonglian Zhang, Metuchen, NJ (US); Sherman T. Waddell, Westfield, NJ (US); Tao Yu, Edison, NJ (US); John A. McCauley, Maple Glen, PA (US); Andrew Stamford, Chatham, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/061,369

(22) PCT Filed: Dec. 12, 2016

(86) PCT No.: PCT/US2016/066078
§ 371 (c)(1),
(2) Date: Jun. 12, 2018

(87) PCT Pub. No.: WO2017/106071
PCT Pub. Date: Jun. 22, 2017

(65) Prior Publication Data
US 2019/0040076 A1 Feb. 7, 2019

Related U.S. Application Data

(60) Provisional application No. 62/267,500, filed on Dec. 15, 2015.

(51) Int. Cl.
| | |
|---|---|
| *A61K 31/4375* | (2006.01) |
| *A61K 31/502* | (2006.01) |
| *A61K 31/503* | (2006.01) |
| *A61K 31/34* | (2006.01) |
| *C07D 455/02* | (2006.01) |
| *C07D 491/20* | (2006.01) |
| *A61P 31/18* | (2006.01) |
| *A61K 31/427* | (2006.01) |
| *A61K 31/52* | (2006.01) |
| *A61K 31/505* | (2006.01) |
| *A61K 31/506* | (2006.01) |
| *A61K 31/662* | (2006.01) |

(52) U.S. Cl.
CPC ............ *C07D 491/20* (2013.01); *A61K 31/34* (2013.01); *A61K 31/427* (2013.01); *A61K 31/4375* (2013.01); *A61K 31/505* (2013.01); *A61K 31/506* (2013.01); *A61K 31/52* (2013.01); *A61K 31/662* (2013.01); *A61P 31/18* (2018.01)

(58) Field of Classification Search
CPC ... A61P 31/18; A61K 31/4375; A61K 31/502; A61K 31/503; A61K 31/34; C07D 455/02; C07D 491/20
USPC .......... 546/138, 183, 121, 122, 18; 549/344; 514/278, 306, 300, 462
See application file for complete search history.

(56) References Cited

U.S. PATENT DOCUMENTS

| | | |
|---|---|---|
| 6,630,488 B1 | 10/2003 | Lamothe et al. |
| 2012/0220571 A1 | 8/2012 | Wai et al. |
| 2015/0329539 A1 | 11/2015 | Embrey et al. |
| 2016/0228419 A1 | 8/2016 | Yu et al. |
| 2016/0317543 A1 | 11/2016 | Graham et al. |
| 2017/0334924 A1 | 11/2017 | Embrey et al. |
| 2017/0362252 A1 | 12/2017 | Graham et al. |
| 2018/0051043 A1 | 2/2018 | Yu et al. |

FOREIGN PATENT DOCUMENTS

WO 2015048363 A1 4/2015

OTHER PUBLICATIONS

International Search Report and Written Opinion for PCT/US2016/066078 dated Feb. 17, 2017, 9 pages.

*Primary Examiner* — Matthew P Coughlin
*Assistant Examiner* — Sagar Patel
(74) *Attorney, Agent, or Firm* — Nicole M. Beeler; John C. Todaro

(57) ABSTRACT

The present invention relates to spirocyclic quinolizine derivatives and pharmaceutically acceptable salts or prodrug thereof, compositions comprising at least one spirocyclic quinolizine derivative, and methods of using the spirocyclic quinolizine derivatives for treating or preventing HIV infection in a subject.

19 Claims, No Drawings

SPIROCYCLIC QUINOLIZINE DERIVATIVES USEFUL AS HIV INTEGRASE INHIBITORS

CROSS REFERENCE TO RELATED APPLICATIONS

This application is a U.S. National Phase application under 35 U.S.C. § 371 of PCT Application No. PCT/US2016/066078 filed Dec. 12, 2016, which claims priority from US Ser. No. 62/267,500 filed Dec. 15, 2015.

FIELD OF THE INVENTION

The present invention relates to Spirocyclic Quinolizine Derivatives, compositions comprising at least one Spirocyclic Quinolizine Derivative, and methods of using the Spirocyclic Quinolizine Derivatives for treating or preventing HIV infection in a subject.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Rather, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

The following references may be of interest as background:

International Publication Nos. WO 11/045330 and WO 11/121105 disclose macrocyclic compounds having HIV integrase inhibitory activity.

Kinzel et al., *Tet. Letters* 2007, 48(37): pp. 6552-6555 discloses the synthesis of tetrahydropyridopyrimidones as a scaffold for HIV-1 integrase inhibitors.

Ferrara et al., *Tet. Letters* 2007, 48(37), pp. 8379-8382 discloses the synthesis of a hexahydropyrimido[1,2-a] azepine-2-carboxamide derivative useful as an HIV integrase inhibitor.

Muraglia et al., *J. Med. Chem.* 2008, 51: 861-874 discloses the design and synthesis of bicyclic pyrimidinones as potent and orally bioavailable HIV-1 integrase inhibitors.

US2004/229909 discloses certain compounds having integrase inhibitory activity.

U.S. Pat. No. 7,232,819 and US 2007/0083045 disclose certain 5,6-dihydroxypyrimidine-4-carboxamides as HIV integrase inhibitors.

U.S. Pat. Nos. 7,169,780, 7,217,713, and US 2007/0123524 disclose certain N-substituted 5-hydroxy-6-oxo-1,6-dihydropyrimidine-4-carboxamides as HIV integrase inhibitors.

U.S. Pat. No. 7,279,487 discloses certain hydroxynaphthyridinone carboxamides that are useful as HIV integrase inhibitors.

U.S. Pat. Nos. 7,135,467 and 7,037,908 disclose certain pyrimidine carboxamides that are useful as HIV integrase inhibitors.

U.S. Pat. No. 7,211,572 discloses certain nitrogenous condensed ring compounds that are HIV integrase inhibitors.

U.S. Pat. No. 7,414,045 discloses certain tetrahydro-4H-pyrido[1,2-a]pyrimidine carboxamides, hexahydropyrimido[1,2-a]azepine carboxamides, and related compounds that are useful as HIV integrase inhibitors.

U.S. Pat. No. 8,129,385 discloses certain hexahydro-2H-pyrido[1',2':4,5]pyrazino[2,1-b][1,3]oxazine-9-carboxamides, and related compounds that are useful as HIV integrase inhibitors.

WO 2006/103399 discloses certain tetrahydro-4H-pyrimidooxazepine carboaxmides, tetrahydropyrazinopyrimidine carboxamides, hexahydropyrimidodiazepine carboxamides, and related compounds that are useful as HIV integrase inhibitors.

US 2007/0142635 discloses processes for preparing hexahydropyrimido[1,2-a]azepine-2-carboxylates and related compounds.

US 2007/0149556 discloses certain hydroxypyrimidinone derivatives having HIV integrase inhibitory activity.

Various pyrimidinone compounds useful as HIV integrase inhibitors are also disclosed in U.S. Pat. Nos. 7,115,601, 7,157,447, 7,173,022, 7,176,196, 7,192,948, 7,273,859, and U.S. Pat. No. 7,419,969.

US 2007/0111984 discloses a series of bicyclic pyrimidinone compounds useful as HIV integrase inhibitors.

US 2006/0276466, US 2007/0049606, US 2007/0111985, US 2007/0112190, US 2007/0281917, US 2008/0004265 each disclose a series of bicyclic pyrimidinone compounds useful as HIV integrase inhibitors.

SUMMARY OF THE INVENTION

In one aspect, the present invention provides Compounds of Formula (I):

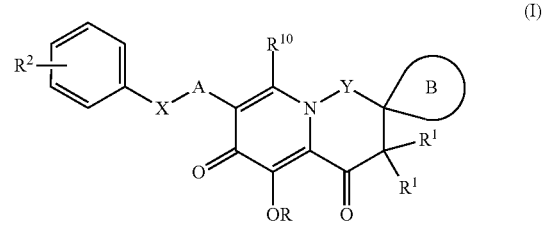

or a pharmaceutically acceptable salt or prodrug thereof, wherein:

A is —NHC(O)— or 5 or 6-membered monocyclic heteroaryl;

B is 3 to 8-membered monocyclic heterocycloalkyl, which may be optionally substituted with one or more groups, each independently selected from $R^6$;

X is $C_1$-$C_3$ alkylene;

Y is —$CH_2$—, —$CH(R^6)$— or —$N(R^3)$—;

R is H or benzyl;

each occurrence of $R^1$ is independently selected from H, $C_1$-$C_6$ alkyl, $C_1$-$C_6$ haloalkyl, $C_2$-$C_6$ alkenyl, —($C_1$-$C_6$ alkylene)-O—($C_1$-$C_6$ alkyl), —($C_1$-$C_6$ alkylene)$_m$-Z—($C_1$-$C_3$ alkylene)$_m$-$R^{11}$, —$N(R^{11})_2$ and —$OR^7$, or both $R^1$ groups and the common carbon atom to which they are attached, join to form an exocyclic olefin group having the formula:

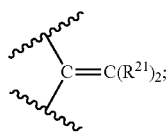

$R^2$ represents up to 3 optional substituents, each independently selected from halo, $C_1$-$C_6$ alkyl, —O—($C_1$-$C_6$ alkyl) and $C_1$-$C_6$ haloalkyl;

$R^3$ is selected from H, $C_1$-$C_6$ alkyl, —$SO_2R^4$, —$C(O)R^4$, —($C_1$-$C_6$ alkylene)$_m$-$C(O)N(R^5)_2$, —($C_2$-$C_4$ alkylene)-O—($C_1$-$C_6$ alkyl), —($C_2$-$C_4$ alkylene)-S—($C_1$-$C_6$ alkyl), —($C_2$-$C_4$ alkylene)-$SO_2$—($C_1$-$C_6$ alkyl), —($C_2$-$C_4$ alkylene)-N—($C_1$-$C_6$ alkyl)$_2$, —($C_1$-$C_6$ alkylene)-Z—($C_1$-$C_3$ alkylene)$_m$-$R^{11}$, $C_3$-$C_7$ cycloalkyl, phenyl, 4 to 8-membered monocyclic heterocycloalkyl, 6-membered monocyclic heteroaryl and 8 to 10-membered bicyclic heteroaryl;

each occurrence of $R^4$ is independently selected from H, $C_1$-$C_6$ alkyl, $C_1$-$C_6$ haloalkyl, $C_3$-$C_7$ cycloalkyl, phenyl, 3 to 8-embered monocyclic heterocycloalkyl, 6-membered monocyclic heteroaryl and 8 to 10-membered bicyclic heteroaryl, wherein said $C_3$-$C_7$ cycloalkyl group, said phenyl group, said 3 to 8-membered monocyclic heteroaryl group, said 6-membered monocyclic heteroaryl group and said 8 to 10-membered bicyclic heteroaryl group may be optionally substituted with one or more groups, each independently selected from $R^6$;

each occurrence of $R^5$ is independently selected from H, $C_1$-$C_6$ alkyl, $C_3$-$C_7$ cycloalkyl, —($C_1$-$C_6$ alkylene)-$N(R^7)_2$, $C_1$-$C_6$ haloalkyl, —$C(O)O(C_1$-$C_6$ alkyl), —($C_1$-$C_6$ alkylene)$_m$-Z—($C_1$-$C_3$ alkylene)$_m$-$R^{11}$, —($C_1$-$C_6$ alkylene)$_m$-$R^8$ and —($C_1$-$C_6$ alkylene)-O—($C_1$-$C_6$ alkyl);

each occurrence of $R^6$ is independently selected from halo, $C_1$-$C_6$ alkyl, $C_1$-$C_6$ haloalkyl, —($C_1$-$C_6$ alkylene)$_m$-Z—($C_1$-$C_3$ alkylene)$_m$-$R^{11}$, —$N(R^{20})_2$, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)-O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —$S(O)_2(C_1$-$C_6$ alkyl), —$NHS(O)_2$—($C_1$-$C_6$ alkyl), —$S(O)_2NH$—($C_1$-$C_6$ alkyl), —$OC(O)$—($C_1$-$C_6$ haloalkyl), —($C_1$-$C_6$ alkylene)$_m$-C(O)O—($C_1$-$C_6$ alkyl), —($C_1$-$C_6$ alkylene)$_m$-C(O)—($C_1$-$C_6$ alkyl), —($C_1$-$C_6$ alkylene)$_m$-C(O)N($R^7$)$_2$, $C_1$-$C_6$ hydroxyalkyl, —$P(O)(OR^9)_2$ and —CN;

each occurrence of $R^7$ is independently selected from H, $C_1$-$C_6$ alkyl, $C_3$-$C_7$ cycloalkyl, $C_1$-$C_6$ haloalkyl, —C(O)O($C_1$-$C_6$ alkyl), —($C_1$-$C_6$ alkylene)$_m$-Z—($C_1$-$C_3$ alkylene)$_m$-$R^{11}$, —($C_1$-$C_6$ alkylene)$_m$-$R^8$ and —($C_1$-$C_6$ alkylene)-O—($C_1$-$C_6$ alkyl);

each occurrence of $R^8$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^9$ is independently selected from H, $C_1$-$C_6$ alkyl and —($C_1$-$C_6$ alkylene)$_m$-Z—($C_1$-$C_3$ alkylene)$_m$-$R^{11}$;

$R^{10}$ is selected from H, $C_1$-$C_6$ alkyl, $C_3$-$C_7$ cycloalkyl and —($C_1$-$C_4$ alkylene)-O—($C_1$-$C_6$ alkyl);

each occurrence of is independently selected from —P(O)(—$OR^{18}$)$_2$,

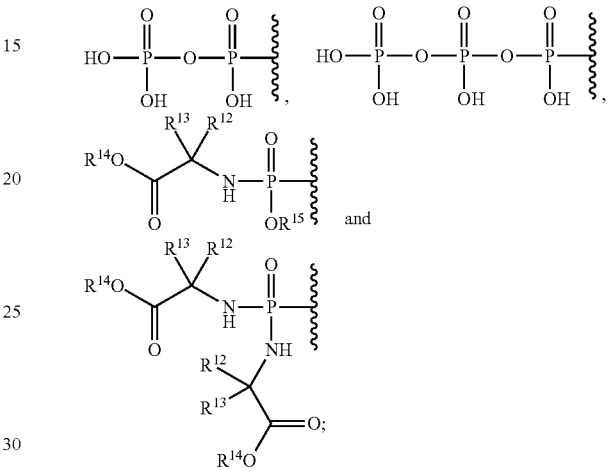

each occurrence of $R^{12}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —$OR^{16}$, —$SR^{16}$, guanidino, —$N(R^{16})_2$, —$C(O)OR^{16}$, —$C(O)N(R^{16})_2$, —$NHC(O)R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —$OR^{16}$;

each occurrence of $R^{13}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —$OR^{16}$, —$SR^{16}$, guanidino, —$N(R^{16})_2$, —$C(O)OR^{16}$, —$C(O)N(R^{16})_2$, —$NHC(O)R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —$OR^{16}$;

each occurrence of $R^{14}$ is independently selected from H, $C_1$-$C_{20}$ alkyl, $C_2$-$C_{20}$ alkenyl, —($C_1$-$C_3$ alkylene)$_m$-($C_3$-$C_7$ cycloalkyl), —($C_1$-$C_3$ alkylene)$_m$-($C_6$-$C_{10}$ aryl) or —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group may be optionally substituted with up to three groups, each independently selected from halo, —$OR^{16}$, —$C(O)OR^{16}$, CN, $NO_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —$N(R^{16})_2$, —$C(O)N(R^{16})_2$—$SR^{16}$, —$S(O)R^{16}$, —$S(O)_2R^{16}$, —$S(O)_2N(R^{16})_2$, —$NHC(O)R^{16}$, —NHC(O)$OR^{16}$ and —$NHC(O)N(R^{16})_2$;

$R^{15}$ is selected from H, $C_6$-$C_{10}$ aryl, 5- or 6-membered monocyclic heteroaryl and 9- or 10-membered bicyclic heteroaryl, wherein said $C_6$-$C_{10}$ aryl group, said 5- or 6-membered monocyclic heteroaryl group and said 9- or 10-membered bicyclic heteroaryl group may be optionally substituted with $R^{17}$;

each occurrence of $R^{16}$ is independently selected from H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group may be optionally substituted with $R^{17}$;

$R^{17}$ represents from one to five substituent groups, each independently selected from $C_1$-$C_6$ alkyl, halo, —$OR^{19}$, —$SR^{19}$, $C_1$-$C_6$ haloalkyl, $C_1$-$C_6$ hydroxyalkyl, —O—($C_1$-$C_6$ haloalkyl), —CN, —$NO_2$, —$N(R^{19})_2$, —$C(O)OR^{19}$, —$C(O)N(R^{19})_2$ and —$NHC(O)R^{19}$;

each occurrence of $R^{18}$ is independently selected from H, $C_1$-$C_6$ alkyl, $C_6$-$C_{10}$ aryl, —($C_1$-$C_6$ alkylene)-O—($C_1$-$C_{20}$ alkyl), —($C_1$-$C_6$ alkylene)-O—C(O)—$R^{16}$, and —($C_1$-$C_6$ alkylene)-O—C(O)—O—$R^{16}$;

each occurrence of $R^{19}$ is independently selected from H, $C_1$-$C_{10}$ alkyl, $C_1$-$C_6$ haloalkyl, $C_1$-$C_6$ hydroxyalkyl, alkylene)$_m$-($C_3$-$C_7$ cycloalkyl), alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl);

each occurrence of $R^{20}$ is independently selected from H, $C_1$-$C_6$ alkyl and —($C_1$-$C_6$ alkylene)$_m$-Z—($C_1$-$C_3$ alkylene)$_m$-$R^{11}$;

each occurrence of $R^{21}$ is independently selected from H and $C_1$-$C_6$ alkyl;

each occurrence of Z is independently selected from a bond, —O— or —$N(R^9)$—;

each occurrence of m is independently 0 or 1; and n is 1 or 2.

The Compounds of Formula (I) (also referred to herein as the "Spirocyclic Quinolizine Derivatives") and pharmaceutically acceptable salts or prodrugs thereof may be useful, for example, for inhibiting HIV viral replication or replicon activity, or for treating or preventing HIV infection in a subject. Without being bound by any specific theory, it is believed that the Spirocyclic Quinolizine Derivatives inhibit HIV viral replication by inhibiting HIV Integrase.

Accordingly, the present invention provides methods for treating or preventing HIV infection in a subject, comprising administering to the subject an effective amount of at least one Spirocyclic Quinolizine Derivative.

The details of the invention are set forth in the accompanying detailed description below.

Although any methods and materials similar to those described herein may be used in the practice or testing of the present invention, illustrative methods and materials are now described. Other embodiments, aspects and features of the present invention are either further described in or will be apparent from the ensuing description, examples and appended claims.

DETAILED DESCRIPTION OF THE INVENTION

The present invention includes Spirocyclic Quinolizine Derivatives, compositions comprising at least one Spirocyclic Quinolizine Derivative, and methods of using the Spirocyclic Quinolizine Derivatives for treating or preventing HIV infection in a subject.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "—O-alkyl," etc. . . .

As used herein, and throughout this disclosure, the following terms, unless otherwise indicated, shall be understood to have the following meanings:

A "subject" is a human or non-human mammal. In one embodiment, a subject is a human. In another embodiment, a subject is a primate. In another embodiment, a subject is a monkey. In another embodiment, a subject is a chimpanzee. In still another embodiment, a subject is a rhesus monkey.

The term "effective amount" as used herein, refers to an amount of Spirocyclic Quinolizine Derivative and/or an additional therapeutic agent, or a composition thereof that is effective in inhibiting HIV replication and in producing the desired therapeutic, ameliorative, inhibitory or preventative effect when administered to a subject suffering from HIV infection or AIDS. In the combination therapies of the present invention, an effective amount can refer to each individual agent or to the combination as a whole, wherein the amounts of all agents administered are together effective, but wherein the component agent of the combination may not be present individually in an effective amount.

The term "preventing," as used herein with respect to an HIV viral infection or AIDS, refers to reducing the likelihood or severity of HIV infection or AIDS.

The term "alkyl," as used herein, refers to an aliphatic hydrocarbon group having one of its hydrogen atoms replaced with a bond. An alkyl group may be straight or branched and contain from about 1 to about 20 carbon atoms. In one embodiment, an alkyl group contains from about 1 to about 12 carbon atoms. In different embodiments, an alkyl group contains from 1 to 6 carbon atoms ($C_1$-$C_6$ alkyl) or from about 1 to about 4 carbon atoms ($C_1$-$C_4$ alkyl). Non-limiting examples of alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —$NH_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. In one embodiment, an alkyl group is linear. In another embodiment, an alkyl group is branched. Unless otherwise indicated, an alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms. Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkynyl" refers to an alkynyl group having from 2 to 6 carbon atoms. Unless otherwise indicated, an alkynyl group is unsubstituted.

The term "alkylene," as used herein, refers to an alkyl group, as defined above, wherein one of the alkyl group's hydrogen atoms has been replaced with a bond. Non-limiting examples of alkylene groups include —CH$_2$—, —CH$_2$CH$_2$—, —CH$_2$CH$_2$CH$_2$—, —CH$_2$CH$_2$CH$_2$CH$_2$—, —CH(CH$_3$)CH$_2$CH$_2$—, —CH(CH$_3$)— and —CH$_2$CH(CH$_3$)CH$_2$—. In one embodiment, an alkylene group has from 1 to about 6 carbon atoms. In another embodiment, an alkylene group has from about 3 to about 5 carbon atoms. In another embodiment, an alkylene group is branched. In another embodiment, an alkylene group is linear. In one embodiment, an alkylene group is —CH$_2$—. The term "C$_1$-C$_6$ alkylene" refers to an alkylene group having from 1 to 6 carbon atoms. The term "C$_2$-C$_4$ alkylene" refers to an alkylene group having from 2 to 4 carbon atoms.

The term "alkenylene," as used herein, refers to an alkenyl group, as defined above, wherein one of the alkenyl group's hydrogen atoms has been replaced with a bond. Non-limiting examples of alkenylene groups include —CH═CH—, —CH═CHCH$_2$—, —CH$_2$CH═CH—, —CH$_2$CH═CHCH$_2$—, —CH═CHCH$_2$CH$_2$—, —CH$_2$CH$_2$CH═CH— and —CH(CH$_3$)CH═CH—. In one embodiment, an alkenylene group has from 2 to about 6 carbon atoms. In another embodiment, an alkenylene group has from about 3 to about 5 carbon atoms. In another embodiment, an alkenylene group is branched. In another embodiment, an alkenylene group is linear. The term "C$_2$-C$_6$ alkylene" refers to an alkenylene group having from 2 to 6 carbon atoms. The term "C$_3$-C$_5$ alkenylene" refers to an alkenylene group having from 3 to 5 carbon atoms.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group may be optionally substituted with one or more "ring system substituents" which may be the same or different, and are as defined herein below. In one embodiment, an aryl group may be optionally fused to a cycloalkyl or cycloalkanoyl group. Non-limiting examples of aryl groups include phenyl and naphthyl. In one embodiment, an aryl group is phenyl. Unless otherwise indicated, an aryl group is unsubstituted.

The term "arylene," as used herein, refers to a bivalent group derived from an aryl group, as defined above, by removal of a hydrogen atom from a ring carbon of an aryl group. An arylene group may be derived from a monocyclic or multicyclic ring system comprising from about 6 to about 14 carbon atoms. In one embodiment, an arylene group contains from about 6 to about 10 carbon atoms. In another embodiment, an arylene group is a naphthylene group. In another embodiment, an arylene group is a phenylene group. An arylene group may be optionally substituted with one or more "ring system substituents" which may be the same or different, and are as defined herein below. An arylene group is divalent and either available bond on an arylene group can connect to either group flanking the arylene group. For example, the group "A-arylene-B," wherein the arylene group is:

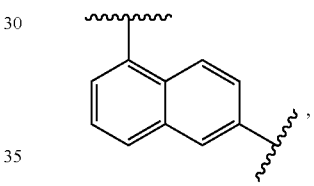

is understood to represent both:

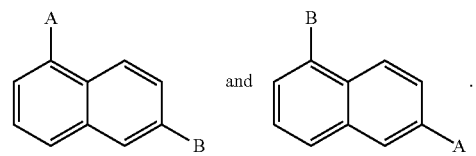

In one embodiment, an arylene group may be optionally fused to a cycloalkyl or cycloalkanoyl group. Non-limiting examples of arylene groups include phenylene and naphthalene. In one embodiment, an arylene group is unsubstituted. In another embodiment, an arylene group is:

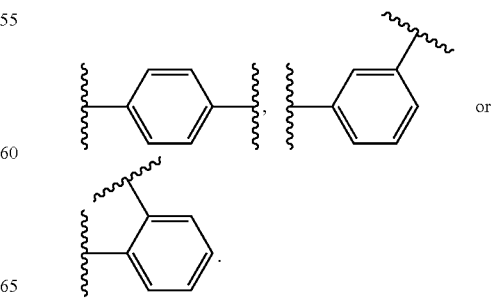

Unless otherwise indicated, an arylene group is unsubstituted.

The term "cycloalkyl," as used herein, refers to a saturated or unsaturated non-aromatic mono- or multicyclic ring system comprising from about 3 to about 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group, as defined above, which is fused to an aryl (e.g., benzene) or heteroaryl ring. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl. A cycloalkyl group may be optionally substituted with one or more "ring system substituents" which may be the same or different, and are as defined herein below. In one embodiment, a cycloalkyl group is unsubstituted. The term "3 to 7-membered cycloalkyl" refers to a cycloalkyl group having from 3 to 7 ring carbon atoms. Unless otherwise indicated, a cycloalkyl group is unsubstituted. A ring carbon atom of a cycloalkyl group may be functionalized as a carbonyl group. An illustrative example of such a cycloalkyl group (also referred to herein as a "cycloalkanoyl" group) includes, but is not limited to, cyclobutanoyl:

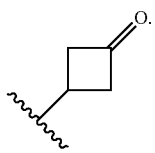

The term "halo," as used herein, means —F, —Cl, —Br or —I.

The term "haloalkyl," as used herein, refers to an alkyl group as defined above, wherein one or more of the alkyl group's hydrogen atoms has been replaced with a halogen. In one embodiment, a haloalkyl group has from 1 to 6 carbon atoms. In another embodiment, a haloalkyl group is substituted with from 1 to 3 F atoms. Non-limiting examples of haloalkyl groups include —$CH_2F$, —$CHF_2$, —$CF_3$, —$CH_2Cl$ and —$CCl_3$. The term "$C_1$-$C_6$ haloalkyl" refers to a haloalkyl group having from 1 to 6 carbon atoms.

The term "hydroxyalkyl," as used herein, refers to an alkyl group as defined above, wherein one or more of the alkyl group's hydrogen atoms have been replaced with an OH group. In one embodiment, a hydroxyalkyl group has from 1 to 6 carbon atoms. Non-limiting examples of hydroxyalkyl groups include —$CH_2OH$, —$CH_2CH_2OH$, —$CH_2CH_2CH_2OH$ and —$CH_2CH(OH)CH_3$. The term "$C_1$-$C_6$ hydroxyalkyl" refers to a hydroxyalkyl group having from 1 to 6 carbon atoms.

The term "heteroaryl," as used herein, refers to an aromatic monocyclic or multicyclic ring system comprising about 5 to about 14 ring atoms, wherein from 1 to 4 of the ring atoms is independently O, N or S and the remaining ring atoms are carbon atoms. In one embodiment, a heteroaryl group has 5 to 10 ring atoms. In another embodiment, a heteroaryl group is monocyclic and has 5 or 6 ring atoms. In another embodiment, a heteroaryl group is bicyclic. In another embodiment, a heteroaryl group is bicyclic and has 9 or 10 ring atoms. A heteroaryl group may be optionally substituted by one or more "ring system substituents" which may be the same or different, and are as defined herein below. A heteroaryl group is joined via a ring carbon atom, and any nitrogen atom of a heteroaryl may be optionally oxidized to the corresponding N-oxide. The term "heteroaryl" also encompasses a heteroaryl group, as defined above, which is fused to a benzene ring. Non-limiting examples of heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, benzimidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like, and all isomeric forms thereof. The term "heteroaryl" also refers to partially saturated heteroaryl moieties such as, for example, tetrahydroisoquinolyl, tetrahydroquinolyl and the like. In one embodiment, a heteroaryl group is a 5-membered heteroaryl. In another embodiment, a heteroaryl group is a 6-membered monocyclic heteroaryl. In another embodiment, a heteroaryl group comprises a 5- to 6-membered monocyclic heteroaryl group fused to a benzene ring. Unless otherwise indicated, a heteroaryl group is unsubstituted.

The term "heterocycloalkyl," as used herein, refers to a non-aromatic saturated monocyclic or multicyclic ring system comprising 3 to about 11 ring atoms, wherein from 1 to 4 of the ring atoms are independently O, S, N or Si, and the remainder of the ring atoms are carbon atoms. A heterocycloalkyl group may be joined via a ring carbon, ring silicon atom or ring nitrogen atom. In one embodiment, a heterocycloalkyl group is monocyclic and has from about 3 to about 7 ring atoms. In another embodiment, a heterocycloalkyl group is monocyclic has from about 5 to about 8 ring atoms. In another embodiment, a heterocycloalkyl group is bicyclic and has from about 8 to about 11 ring atoms. In still another embodiment, a heterocycloalkyl group is monocyclic and has 5 or 6 ring atoms. In one embodiment, a heterocycloalkyl group is monocyclic. In another embodiment, a heterocycloalkyl group is bicyclic. There are no adjacent oxygen and/or sulfur atoms present in the ring system. Any —NH group in a heterocycloalkyl ring may exist protected such as, for example, as an —N(BOC), —N(Cbz), —N(Tos) group and the like; such protected heterocycloalkyl groups are considered part of this invention. The term "heterocycloalkyl" also encompasses a heterocycloalkyl group, as defined above, which is fused to an aryl (e.g., benzene) or heteroaryl ring. A heterocycloalkyl group may be optionally substituted by one or more "ring system substituents" which may be the same or different, and are as defined herein below. The nitrogen or sulfur atom of the heterocycloalkyl may be optionally oxidized to the corresponding N-oxide, S-oxide or S,S-dioxide. Non-limiting examples of monocyclic heterocycloalkyl rings include oxetanyl, piperidyl, pyrrolidinyl, piperazinyl, morpholinyl, thiomorpholinyl, thiazolidinyl, 1,4-dioxanyl, tetrahydrofuranyl, tetrahydrothiophenyl, delta-lactam, delta-lactone and the like, and all isomers thereof.

A ring carbon atom of a heterocycloalkyl group may be functionalized as a carbonyl group. An illustrative example of such a heterocycloalkyl group is:

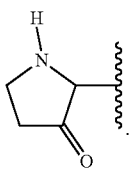

In one embodiment, a heterocycloalkyl group is a 5-membered monocyclic heterocycloalkyl. In another embodiment, a heterocycloalkyl group is a 6-membered monocyclic heterocycloalkyl. The term "4 to 7-membered monocyclic heterocycloalkyl" refers to a monocyclic heterocycloalkyl group having from 4 to 7 ring atoms. The term "5 to 8-membered monocyclic heterocycloalkyl" refers to a monocyclic heterocycloalkyl group having from 5 to 8 ring atoms. The term "8 to 11-membered bicyclic heterocycloalkyl" refers to a bicyclic heterocycloalkyl group having from 8 to 11 ring atoms. Unless otherwise indicated, a heterocycloalkyl group is unsubstituted.

The term "heterocycloalkenyl," as used herein, refers to a heterocycloalkyl group, as defined above, which is non-aromatic and contains at least one endocyclic double bond between two adjacent ring atoms. A heterocycloalkenyl group may be joined via a ring carbon, ring silicon atom or ring nitrogen atom. In one embodiment, a heterocycloalkenyl group is monocyclic and has from about 3 to about 7 ring atoms. In another embodiment, a heterocycloalkenyl group is monocyclic has from about 5 to about 8 ring atoms. In another embodiment, a heterocycloalkenyl group is bicyclic and has from about 8 to about 11 ring atoms. In still another embodiment, a heterocycloalkenyl group is monocyclic and has 5 or 6 ring atoms. In one embodiment, a heterocycloalkenyl group is monocyclic. In another embodiment, a heterocycloalkenyl group is bicyclic. There are no adjacent oxygen and/or sulfur atoms present in the ring system. Any —NH group in a heterocycloalkenyl ring may be substituted or may exist protected such as, for example, as an —N(BOC), —N(Cbz), —N(Tos) group and the like; such protected heterocycloalkenyl groups are considered part of this invention. The term "heterocycloalkenyl" also encompasses a heterocycloalkenyl group, as defined above, which is fused to an aryl (e.g., benzene) or heteroaryl ring. A heterocycloalkenyl group may be optionally substituted by one or more "ring system substituents" which may be the same or different, and are as defined herein below. The nitrogen or sulfur atom of the heterocycloalkenyl may be optionally oxidized to the corresponding N-oxide, S-oxide or S,S-dioxide.

A ring carbon atom of a heterocycloalkenyl group may be functionalized as a carbonyl group. An illustrative example of such a heterocycloalkenyl group is:

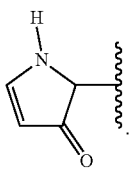

In one embodiment, a heterocycloalkenyl group is a 5-membered monocyclic heterocycloalkenyl. In another embodiment, a heterocycloalkenyl group is a 6-membered monocyclic heterocycloalkenyl. The term "4 to 7-membered monocyclic heterocycloalkenyl" refers to a monocyclic heterocycloalkenyl group having from 4 to 7 ring atoms. The term "5 to 8-membered monocyclic heterocycloalkenyl" refers to a monocyclic heterocycloalkenyl group having from 5 to 8 ring atoms. The term "8 to 11-membered bicyclic heterocycloalkenyl" refers to a bicyclic heterocycloalkenyl group having from 8 to 11 ring atoms. Unless otherwise indicated, a heterocycloalkenyl group is unsubstituted.

The term "ring system substituent," as used herein, refers to a substituent group attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, -alkylene-aryl, -arylene-alkyl, -alkylene-heteroaryl, -alkenylene-heteroaryl, -alkynylene-heteroaryl, —OH, hydroxyalkyl, haloalkyl, —O-alkyl, —O-haloalkyl, -alkylene-O-alkyl, —O-aryl, —O— alkylene-aryl, acyl, —C(O)-aryl, halo, —NO$_2$, —CN, —SF$_5$, —C(O)OH, —C(O)O-alkyl, —C(O)O-aryl, —C(O)O-alkylene-aryl, —S(O)-alkyl, —S(O)$_2$-alkyl, —S(O)-aryl, —S(O)$_2$-aryl, —S(O)-heteroaryl, —S(O)$_2$-heteroaryl, —S-alkyl, —S-aryl, —S-heteroaryl, —S-alkylene-aryl, —S-alkylene-heteroaryl, —S(O)$_2$-alkylene-aryl, —S(O)$_2$-alkylene-heteroaryl, —Si (alkyl)$_2$, —Si(aryl)$_2$, —Si(heteroaryl)$_2$, —Si(alkyl)(aryl), —Si(alkyl)(cycloalkyl), —Si(alkyl)(heteroaryl), cycloalkyl, heterocycloalkyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), —N(Y$_1$)(Y$_2$), -alkylene-N(Y$_1$)(Y$_2$), —C(O)N(Y$_1$)(Y$_2$) and —S(O)$_2$N(Y$_1$)(Y$_2$), wherein Y$_1$ and Y$_2$ may be the same or different and are independently selected from the group consisting of hydrogen, alkyl, aryl, cycloalkyl, and alkylene-aryl. "Ring system substituent" may also mean a single moiety which simultaneously replaces two available hydrogens on two adjacent carbon atoms (one H on each carbon) on a ring system. Examples of such moiety are methylenedioxy, ethylenedioxy, —C(CH$_3$)$_2$— and the like which form moieties such as, for example:

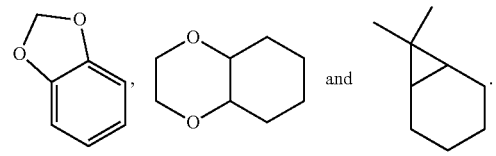

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "in substantially purified form," as used herein, refers to the physical state of a compound after the compound is isolated from a synthetic process (e.g., from a reaction mixture), a natural source, or a combination thereof. The term "in substantially purified form," also refers to the physical state of a compound after the compound is obtained from a purification process or processes described herein or well-known to the skilled artisan (e.g., chromatography, recrystallization and the like), in sufficient purity to be characterizable by standard analytical techniques described herein or well-known to the skilled artisan.

It should also be noted that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, N.Y.

When any substituent or variable (e.g., $R^1$, $R^4$, m, etc.) occurs more than one time in any constituent or in Formula (I), its definition on each occurrence is independent of its definition at every other occurrence, unless otherwise indicated.

As used herein, the term "composition" is intended to encompass a product comprising the specified ingredients in the specified amounts, as well as any product which results from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to provide a Spirocyclic Quinolizine Derivative or a pharmaceutically acceptable salt of the compound. The transformation may occur by various mechanisms (e.g., by metabolic or chemical processes), such as, for example, through hydrolysis in blood. For example, if a Spirocyclic Quinolizine Derivative or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (β-dimethylaminoethyl), carbamoyl-$(C_1-C_2)$alkyl, N,N-di $(C_1-C_2)$alkylcarbamoyl-$(C_1-C_2)$alkyl and piperidino-, pyrrolidino- or morpholino$(C_2-C_3)$alkyl, and the like.

Similarly, if a Spirocyclic Quinolizine Derivative contains an alcohol functional group, a prodrug may be formed by the replacement of one or more of the hydrogen atoms of the alcohol groups with a group such as, for example, $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkyl, α-amino $(C_1-C_4)$alkylene-aryl, arylacyl and α-aminoacyl, or α-aminoacyl-α-aminoacyl, where each α-aminoacyl group is independently selected from the naturally occurring L-amino acids, or glycosyl (the radical resulting from the removal of a hydroxyl group of the hemiacetal form of a carbohydrate).

If a Spirocyclic Quinolizine Derivative incorporates an amine functional group, a prodrug may be formed by the replacement of a hydrogen atom in the amine group with a group such as, for example, R-carbonyl-, RO-carbonyl-, NRR'-carbonyl- wherein R and R' are each independently $(C_1-C_{10})$alkyl, $(C_3-C_7)$ cycloalkyl, benzyl, a natural α-aminoacyl, —C(OH)C(O)OY$^1$ wherein Y$^1$ is H, $(C_1-C_6)$ alkyl or benzyl, —C(OY$^2$)Y$^3$ wherein Y$^2$ is $(C_1-C_4)$ alkyl and Y$^3$ is $(C_1-C_6)$alkyl; carboxy $(C_1-C_6)$alkyl; amino$(C_1-C_4)$alkyl or mono-N- or di-N,N—$(C_1-C_6)$alkylaminoalkyl; —C(Y$^4$)Y$^5$ wherein Y$^4$ is H or methyl and Y$^5$ is mono-N— or di-N,N—$(C_1-C_6)$alkylamino morpholino; piperidin-1-yl or pyrrolidin-1-yl, and the like.

Pharmaceutically acceptable esters of the present compounds include the following groups: (1) carboxylic acid esters obtained by esterification of the hydroxy group of a hydroxyl compound, in which the non-carbonyl moiety of the carboxylic acid portion of the ester grouping is selected from straight or branched chain alkyl (e.g., methyl, ethyl, n-propyl, isopropyl, t-butyl, sec-butyl or n-butyl), alkoxyalkyl (e.g., methoxymethyl), aralkyl (e.g., benzyl), aryloxyalkyl (for example, phenoxymethyl), aryl (e.g., phenyl optionally substituted with, for example, halogen, $C_{1-4}$alkyl, —O—($C_{1-4}$alkyl) or amino); (2) sulfonate esters, such as alkyl- or aralkylsulfonyl (for example, methanesulfonyl); (3) amino acid esters, including those corresponding to both natural and non-natural amino acids (e.g., L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di $(C_{6-24})$acyl glycerol.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of solvates include ethanolates, methanolates, and the like. A "hydrate" is a solvate wherein the solvent molecule is water.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvates, hydrates and the like are described by E. C. van Tonder et al, *AAPS PharmSciTechours.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than room temperature, and cooling the solution at a rate sufficient to form crystals which are then isolated by standard methods. Analytical techniques such as, for example IR spectroscopy, show the presence of the solvent (or water) in the crystals as a solvate (or hydrate).

The Spirocyclic Quinolizine Derivatives can form salts which are also within the scope of this invention. Reference to a Spirocyclic Quinolizine Derivative herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a Spirocyclic Quinolizine Derivative contains both a basic moiety, such as, but not limited to a pyridine or imidazole, and an acidic moiety, such as, but not limited to a carboxylic acid, zwitterions ("inner salts") may be formed and are included within the term "salt(s)" as used herein. In one embodiment, the salt is a pharmaceutically acceptable (i.e., non-toxic, physiologically acceptable) salt. In another embodiment, the salt is other than a pharmaceutically acceptable salt. Salts of the Compounds of Formula (I) may be formed, for example, by reacting a Spirocyclic Quinolizine Derivative with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), arylalkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Diastereomeric mixtures may be separated into their individual diastereomers on the basis of their physical chemical differences by methods well-known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Sterochemically pure compounds may also be prepared by using chiral starting materials or by employing salt resolution techniques. Also, some of the Spirocyclic Quinolizine Derivatives may be atropisomers (e.g., substituted biaryls) and are considered as part of this invention. Enantiomers can also be directly separated using chiral chromatographic techniques.

It is also possible that the Spirocyclic Quinolizine Derivatives may exist in different tautomeric forms, and all such forms are embraced within the scope of the invention. For example, all keto-enol and imine-enamine forms of the compounds are included in the invention.

All stereoisomers (for example, geometric isomers, optical isomers and the like) of the present compounds (including those of the salts, solvates, hydrates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. If a Spirocyclic Quinolizine Derivative incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to apply equally to the salt, solvate, ester and prodrug of enantiomers, stereoisomers, rotamers, tautomers, racemates or prodrugs of the inventive compounds.

In the Compounds of Formula (I), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched Compounds of Formula (I) may be prepared without undue experimentation by conventional techniques well known to those skilled in the art or by processes analogous to those described in the Schemes and Examples herein using appropriate isotopically-enriched reagents and/or intermediates. In one embodiment, a Compound of Formula (I) has one or more of its hydrogen atoms replaced with deuterium.

The Spirocyclic Quinolizine Derivatives are useful in human and veterinary medicine for treating or preventing HIV infection in a subject. In one embodiment, the Spirocyclic Quinolizine Derivatives may be inhibitors of HIV viral replication. In a specific embodiment, the Spirocyclic Quinolizine Derivatives are inhibitors of HIV-1. Accordingly, the Spirocyclic Quinolizine Derivatives are useful for treating HIV infections and AIDS. In accordance with the invention, the Spirocyclic Quinolizine Derivatives may be administered to a subject in need of treatment or prevention of HIV infection.

Accordingly, in one embodiment, the invention provides methods for treating HIV infection in a subject comprising administering to the subject an effective amount of at least one Spirocyclic Quinolizine Derivative or a pharmaceutically acceptable salt thereof. In a specific embodiment, the present invention provides methods for treating AIDS in a subject comprising administering to the subject an effective amount of at least one Spirocyclic Quinolizine Derivative or a pharmaceutically acceptable salt thereof.

The following abbreviations are used herein and have the following meanings: Anal. Is analytical, ACN is acetonitrile, br is broad, calc. is calculated, d is doublet, DCM is dichloromethane, Dess Martin Periodinane is 1,1,1-triacetoxy-1,1-dihydro-1,2-benziodoxol-3(1H)-one; DMF is N,N-dimethylformamide, DMPU is 1,3-dimethyltetrahydropyrimidin-2(1H)-one, DMSO is dimethyl sulfoxide, ESI is electrospray ionization, EtOAc is ethyl acetate, HPLC is high-pressure liquid chromatography, Lawesson's Reagent is 2,4-Bis(4-methoxyphenyl)-1,3,2,4-dithiadiphosphetane-2,4-dithione, LCMS is liquid chromatography-mass spectrometry, m is multiplet, MeI is iodomethane, MeOH is methanol, MS is mass spectrometry, NMR is nuclear magnetic resonance spectroscopy, rt is room temperature, s is singlet, t is triplet, TFA is trifluoroacetic acid, THF is tetrahydrofuran, TLC is thin-layer chromatography, wt % is percentage by weight and Zhan catalyst 1-B is dichloro[1,3-bis(2,4,6-trimethylphenyl)-2-imidazolidinylidene][[5-[(dimethylamino)sulfonyl]-2-(1-methylethoxy-O)phenyl] methylene-C]ruthenium(II).

The Compounds of Formula (I)

The present invention provides Spirocyclic Quinolizine Derivatives of Formula (I):

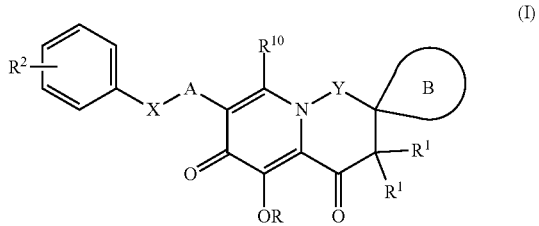

(I)

and pharmaceutically acceptable salts thereof, wherein A, B, X, Y, R, $R^1$, $R^2$ and $R^{10}$ are defined above for the Compounds of Formula (I).

In one embodiment, A is 5 or 6-membered monocyclic heterocycle.

In another embodiment, A is 5-membered monocyclic heterocycle.

In another embodiment, A is thiadiazolyl.

In another embodiment, A is —NHC(O)—.

In one embodiment, X is —CH$_2$—.

In another embodiment, X is —CH(CH$_3$)—.

In one embodiment, Y is —CH($R^6$)—.

In still another embodiment, Y is —N($R^3$)—.

In another embodiment, Y is —N(C$_1$-C$_6$ alkyl)-.

In another embodiment, Y is —N(CH$_3$)—.

In one embodiment, Y is —N($R^3$)— and $R^3$ is —(C$_1$-C$_6$ alkylene)-$R^{11}$.

In another embodiment, Y is —N($R^3$)— and $R^3$ is —(C$_1$-C$_6$ alkylene)-P(O)(—OR$^{18}$)$_2$.

In still another embodiment, Y is —N($R^3$)— and $R^3$ is —(C$_1$-C$_3$ alkylene)-P(O)(—OH)$_2$.

In another embodiment, Y is —N($R^3$)— and $R^3$ is —(C$_1$-C$_3$ alkylene)-P(O)(—OR$^{18}$)$_2$ and each occurrence of $R^{18}$ is C$_1$-C$_6$ alkyl.

In another embodiment, Y is —N($R^3$)— and $R^3$ is —(C$_1$-C$_3$ alkylene)-P(O)(—OR$^{18}$)$_2$ and each occurrence of $R^{18}$ is independently selected from H and —(C$_1$-C$_3$ alkylene)-OC(O)O—(C$_1$-C$_6$ alkyl).

In yet another embodiment, Y is —N($R^3$)— and $R^3$ is —(C$_1$-C$_6$ alkylene)-$R^{11}$ and $R^{11}$ is:

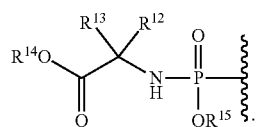

In another embodiment, Y is —N($R^3$)— and $R^3$ is —(C$_1$-C$_6$ alkylene)-$R^{11}$; $R^{11}$ is:

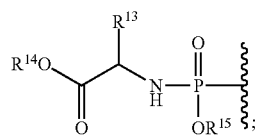

$R^{13}$ is C$_1$-C$_6$ alkyl; $R^{14}$ is C$_1$-C$_6$ alkyl; and $R^{15}$ is phenyl.

In one embodiment, $R^{10}$ is H.

In one embodiment, variables A, B, X, Y, R, $R^1$, $R^2$ and $R^{10}$ for the Compounds of Formula (I) are selected independently of each other.

In another embodiment, the Compounds of Formula (I) are in substantially purified form.

In one embodiment, the compounds of formula (I) have the formula (Ia):

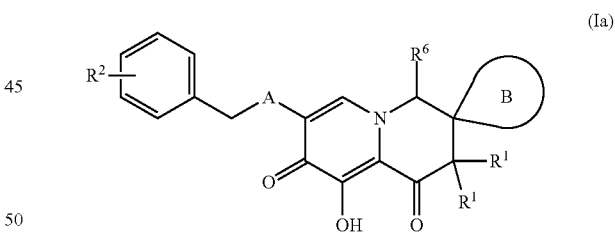

(Ia)

or a pharmaceutically acceptable salt or prodrug thereof, wherein:

A is: —NHC(O)— or:

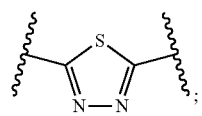

B is a 5 or 6-membered heterocycloalkyl, optionally substituted with $R^6$;

each occurrence of $R^1$ is C$_1$-C$_6$ alkyl, or both $R^1$ groups and the common carbon atom to which they are attached, join to form an exocyclic olefin group having the formula:

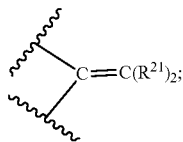

$R^2$ represents up to 3 optional substitutents, each independently selected from halo;

$R^6$ is H or $C_1$-$C_6$ alkyl; and each occurrence of $R^{21}$ is independently selected from H and $C_1$-$C_6$ alkyl.

In one embodiment, for the compounds of formula (I) or (Ia), A is —NHC(O)—.

In another embodiment, embodiment, for the compounds of formula (I) or (Ia), A is:

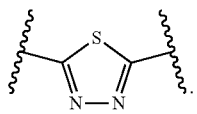

In one embodiment, for the compounds of formula (I) or (Ia), B is 5-membered monocyclic heterocycloalkyl, optionally substituted with $C_1$-$C_6$ alkyl.

In another embodiment, for the compounds of formula (I) or (Ia), B is 6-membered monocyclic heterocycloalkyl, optionally substituted with $C_1$-$C_6$ alkyl.

In another embodiment, for the compounds of formula (I) or (Ia), B is tetrahydrofuranyl, optionally substituted with $C_1$-$C_6$ alkyl.

In still another embodiment, for the compounds of formula (I) or (Ia), B is tetrahydropyranyl, optionally substituted with $C_1$-$C_6$ alkyl.

In one embodiment, for the compounds of formula (I) or (Ia), each occurrence of $R^1$ is independently H or $C_1$-$C_6$ alkyl.

In another embodiment, for the compounds of formula (I) or (Ia), each occurrence of $R^1$ is $C_1$-$C_6$ alkyl.

In another embodiment, for the compounds of formula (I) or (Ia), each occurrence of $R^1$ is methyl.

In one embodiment, for the compounds of formula (I) or (Ia), one occurrence of $R^1$ is —($C_1$-$C_6$ alkylene)$_m$-$R^{11}$.

In another embodiment, for the compounds of formula (I) or (Ia), one occurrence of $R^1$ is —($C_1$-$C_6$ alkylene)$_m$-P(O)(—OR$^{18}$)$_2$.

In still another embodiment, for the compounds of formula (I) or (Ia), one occurrence of $R^1$ is —($C_1$-$C_3$ alkylene)$_m$-P(O)(—OH)$_2$.

In another embodiment, for the compounds of formula (I) or (Ia), one occurrence of $R^1$ is —($C_1$-$C_3$ alkylene)$_m$-P(O)(—OR$^{18}$)$_2$ and each occurrence of $R^{18}$ is $C_1$-$C_6$ alkyl.

In another embodiment, for the compounds of formula (I) or (Ia), one occurrence of $R^1$ is —($C_1$-$C_3$ alkylene)$_m$-P(O)(—OR$^{18}$)$_2$ and each occurrence of $R^{18}$ is independently selected from H and —($C_1$-$C_3$ alkylene)-OC(O)O—($C_1$-$C_6$ alkyl).

In yet another embodiment, for the compounds of formula (I) or (Ia), one occurrence of $R^1$ is —($C_1$-$C_6$ alkylene)-$R^{11}$ and $R^{11}$ is:

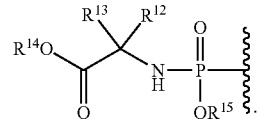

In another embodiment, for the compounds of formula (I) or (Ia), one occurrence of $R^1$ is —($C_1$-$C_6$ alkylene)$_m$-$R^{11}$; $R^{11}$ is

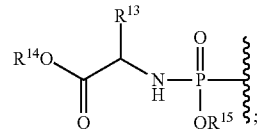

$R^{13}$ is $C_1$-$C_6$ alkyl; $R^{14}$ is $C_1$-$C_6$ alkyl; and $R^{15}$ is phenyl.

In one embodiment, for the compounds of formula (I) or (Ia), each occurrence of $R^1$ is $C_1$-$C_6$ alkyl.

In another embodiment, for the compounds of formula (I) or (Ia), each occurrence of $R^1$ is methyl.

In one embodiment, for the compounds of formula (I) or (Ia), each occurrence of $R^2$ is halo.

In another embodiment, for the compounds of formula (I) or (Ia), $R^2$ represents 3 groups, each independently selected from F and Cl.

In one embodiment, for the compounds of formula (I) or (Ia), one occurrence of $R^6$ is —($C_1$-$C_6$ alkylene)$_m$-$R^{11}$.

In another embodiment, for the compounds of formula (I) or (Ia), one occurrence of $R^6$ is —($C_1$-$C_6$ alkylene)$_m$-P(O)(—OR$^{18}$)$_2$.

In still another embodiment, for the compounds of formula (I) or (Ia), one occurrence of $R^6$ is —($C_1$-$C_3$ alkylene)$_m$-P(O)(—OH)$_2$.

In another embodiment, for the compounds of formula (I) or (Ia), one occurrence of $R^6$ is —($C_1$-$C_3$ alkylene)$_m$-P(O)(—OR$^{18}$)$_2$ and each occurrence of $R^{18}$ is $C_1$-$C_6$ alkyl.

In another embodiment, for the compounds of formula (I) or (Ia), one occurrence of $R^6$ is —($C_1$-$C_3$ alkylene)$_m$-P(O)(—OR$^{18}$)$_2$ and each occurrence of $R^{18}$ is independently selected from H and —($C_1$-$C_3$ alkylene)-OC(O)O—($C_1$-$C_6$ alkyl).

In yet another embodiment, for the compounds of formula (I) or (Ia), one occurrence of $R^6$ is —($C_1$-$C_6$ alkylene)-$R^{11}$ and $R^{11}$ is:

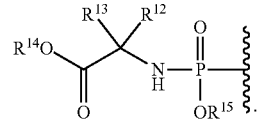

In another embodiment, for the compounds of formula (I) or (Ia), one occurrence of $R^6$ is —($C_1$-$C_6$ alkylene)$_m$-$R^{11}$; $R^{11}$ is:

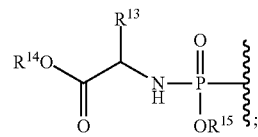

$R^{13}$ is $C_1$-$C_6$ alkyl; $R^{14}$ is $C_1$-$C_6$ alkyl; and $R^{15}$ is phenyl.

In one embodiment, variables A, B, $R^1$, $R^2$ and $R^6$ for the Compounds of Formula (Ia) are selected independently of each other.

In another embodiment, the Compounds of Formula (Ia) are in substantially purified form.

Other embodiments of the present invention include the following:

(a) A pharmaceutical composition comprising an effective amount of a Compound of Formula (I) or a pharmaceutically acceptable salt thereof, and a pharmaceutically acceptable carrier.

(b) The pharmaceutical composition of (a), further comprising a second therapeutic agent selected from the group consisting of HIV antiviral agents, immunomodulators, and anti-infective agents.

(c) The pharmaceutical composition of (b), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(d) A pharmaceutical combination that is (i) a Compound of Formula (I) and (ii) a second therapeutic agent selected from the group consisting of HIV antiviral agents, immunomodulators, and anti-infective agents; wherein the Compound of Formula (I) and the second therapeutic agent are each employed in an amount that renders the combination effective for inhibiting HIV replication, or for treating HIV infection and/or reducing the likelihood or severity of symptoms of HIV infection.

(e) The combination of (d), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(f) A method of inhibiting HIV replication in a subject in need thereof which comprises administering to the subject an effective amount of a Compound of Formula (I).

(g) A method of treating HIV infection and/or reducing the likelihood or severity of symptoms of HIV infection in a subject in need thereof which comprises administering to the subject an effective amount of a Compound of Formula (I).

(h) The method of (g), wherein the Compound of Formula (I) is administered in combination with an effective amount of at least one second therapeutic agent selected from the group consisting of HIV antiviral agents, immunomodulators, and anti-infective agents.

(i) The method of (h), wherein the HIV antiviral agent is an antiviral selected from the group consisting of HIV protease inhibitors, HIV integrase inhibitors, nucleoside reverse transcriptase inhibitors, CCR5 co-receptor antagonists and non-nucleoside reverse-transcriptase inhibitors.

(j) A method of inhibiting HIV replication in a subject in need thereof which comprises administering to the subject the pharmaceutical composition of (a), (b) or (c) or the combination of (d) or (e).

(k) A method of treating HIV infection and/or reducing the likelihood or severity of symptoms of HIV infection in a subject in need thereof which comprises administering to the subject the pharmaceutical composition of (a), (b) or (c) or the combination of (d) or (e).

The present invention also includes a compound of the present invention for use (i) in, (ii) as a medicament for, or (iii) in the preparation of a medicament for: (a) medicine, (b) inhibiting HIV replication or (c) treating HIV infection and/or reducing the likelihood or severity of symptoms of HIV infection. In these uses, the compounds of the present invention can optionally be employed in combination with one or more second therapeutic agents selected from HIV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate. It is understood that references to compounds would include the compound in its present form as well as in different forms, such as polymorphs, solvates and hydrates, as applicable.

It is further to be understood that the embodiments of compositions and methods provided as (a) through (k) above are understood to include all embodiments of the compounds, including such embodiments as result from combinations of embodiments.

The Compounds of Formula (I) may be referred to herein by chemical structure and/or by chemical name. In the instance that both the structure and the name of a Compound of Formula (I) are provided and a discrepancy is found to exist between the chemical structure and the corresponding chemical name, it is understood that the chemical structure will predominate.

Non-limiting examples of the Compounds of Formula (I) include compounds 1-25 as set forth in the Examples below, and pharmaceutically acceptable salts thereof Methods for Making the Compounds of Formula (I)

The Compounds of Formula (I) may be prepared from known or readily prepared starting materials, following methods known to one skilled in the art of organic synthesis. Methods useful for making the Compounds of Formula (I) are set forth in the Examples below and generalized in Schemes 1 and 2 below. Alternative synthetic pathways and analogous structures will be apparent to those skilled in the art of organic synthesis.

Scheme 1 describes a method for making the compounds of formula (I), which corresponds to the bridged tetracyclic 4-pyridinone compounds of Formula (I).

Scheme 1

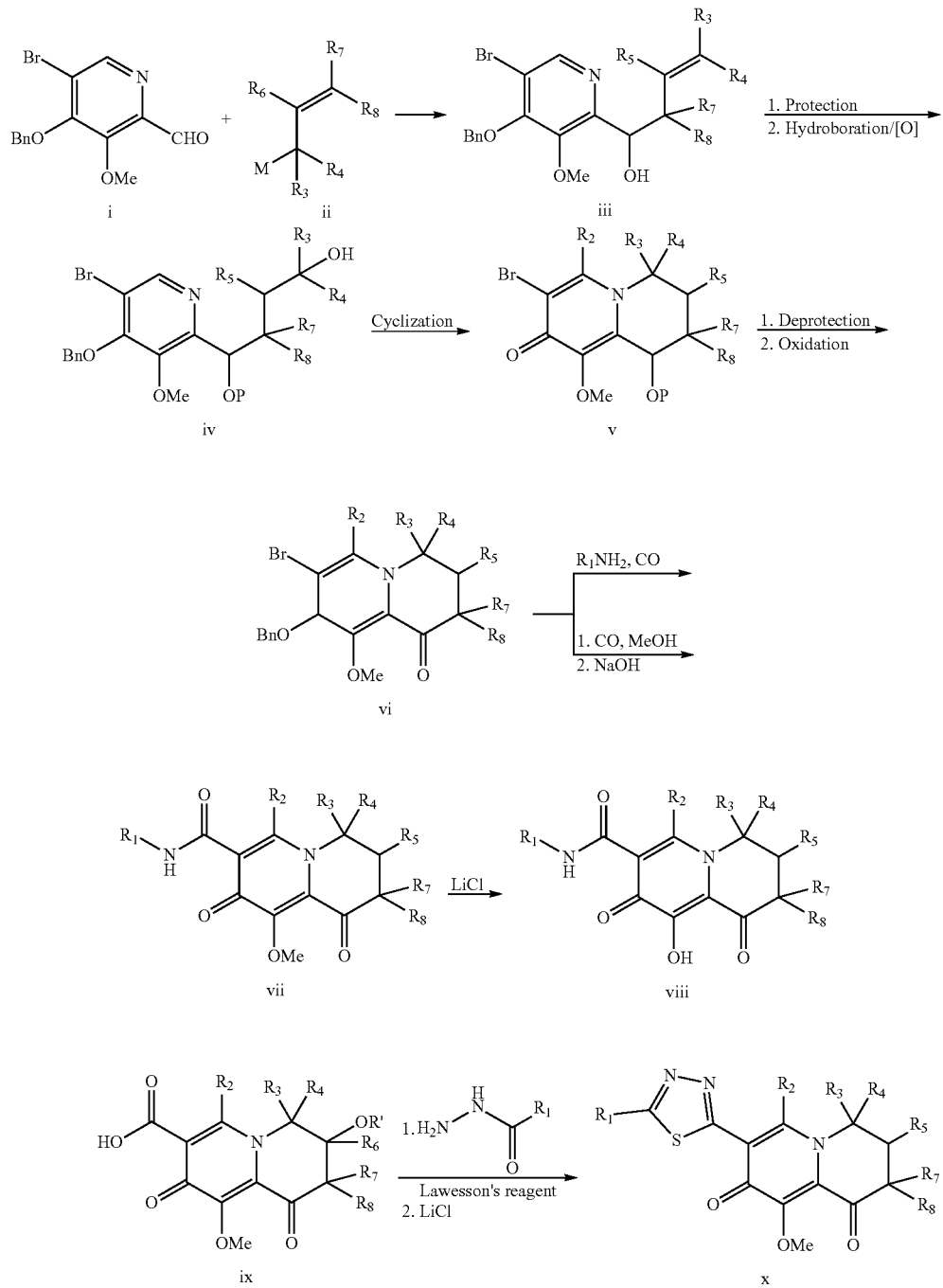

Wherein M is a metal capable of participating in an $S_N2'$ reaction (i.e., Sn, In and Mg).

A pyridyl aldehyde compound of formula i may be reacted with a compound of formula ii to provide a compound of formula iii. The hydroxyl group of iii can then be protected and the olefin oxidized via hydroboration and the corresponding alcohol iv may be subsequently cyclized to provide the bicyclic compounds of formula v. The hydroxyl group of v can then be deprotected and oxidized to provide the bicyclic ketones of formula vi which may be converted to their amide derivatives of formula vii using an amine and carbon monoxide, then reacted with lithium chloride to convert the methoxy group of vii to the corresponding hydroxyl group and provide the compounds of formula viii, which correspond to the compounds of formula (I) wherein X is —NHC(O)—. Alternatively, a compound of formula vi may be oxidized to the carboxylic acids of formula ix which may be subsequently cyclized to provide the 1,3,4-thiadiazole derivatives of formula x, which correspond to the compounds of formula (I), wherein X is 5 or 6-membered heteroaryl.

Scheme 2

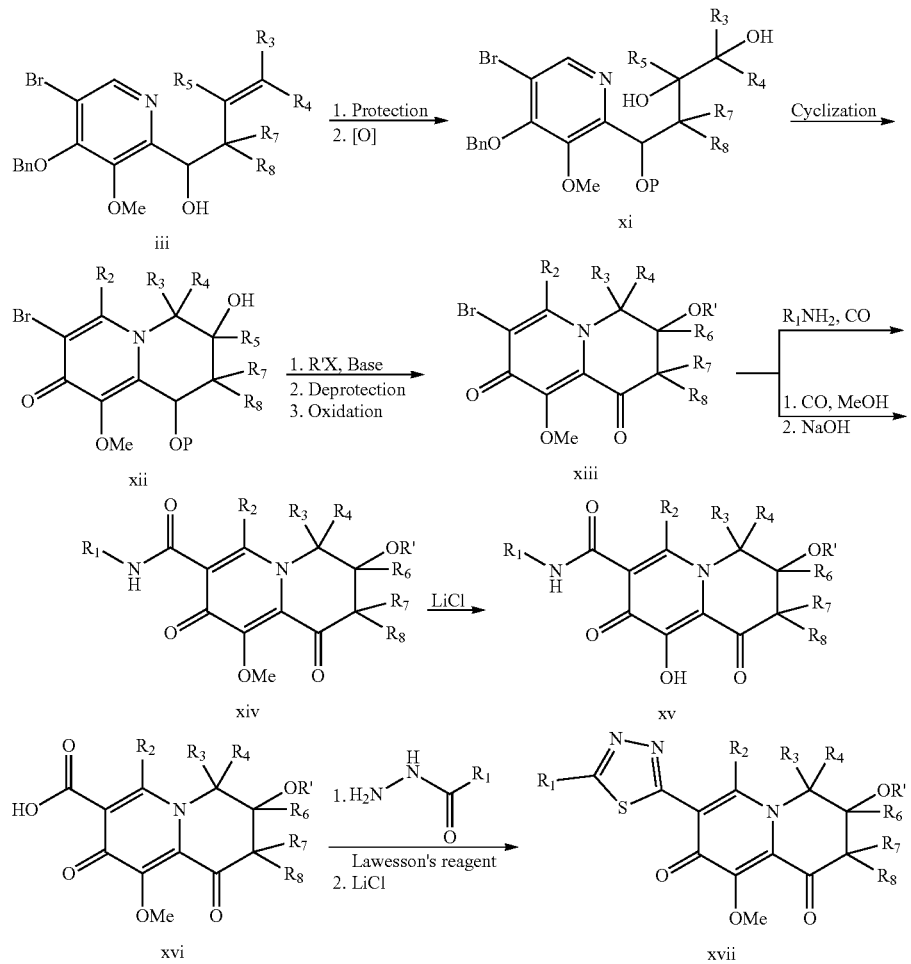

The hydroxyl group of an olefin of formula iii may be protected and the olefin oxidized via to provide the corresponding diols of formula xi, which may be subsequently cyclized to provide the bicyclic compounds of formula xii. A compound of formula xii can then be reacted with an alkyl halide and base to derivatize the free hydroxy group of xii, followed by deprotection and oxidation of the other hydroxyl group to provide the bicyclic ketones of formula xiii. The compounds of formula xiii may be converted to their amide derivatives of formula xiv using an amine and carbon monoxide, then reacted with lithium chloride to convert the methoxy group of xiv to the corresponding hydroxyl group and provide the compounds of formula xv, which correspond to the compounds of formula (I) wherein X is —NHC(O)—. hydroxyl group of v can then be deprotected and oxidized to provide the bicyclic ketones of formula vii which may be reacted with lithium chloride to convert the methoxy group of vii to hydroxyl group and provide the compounds of formula viii, which correspond to the compounds of formula (I) wherein X is —NHC(O)— and $R^3$ is —$OR^7$. Alternatively, a compound of formula xii may be oxidized to the carboxylic acids of formula xvi which may be subsequently cyclicized to provide the 1,3, 4-thiadiazole derivatives of formula xvii, which correspond to the compounds of formula (I), wherein X is 5 or 6-membered heteroaryl and $R^3$ is —$OR^7$.

In the methods for preparing compounds of the present invention set forth in the foregoing schemes, functional groups in various moieties and substituents (in addition to those already explicitly noted in the foregoing schemes) may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection may be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, $3^{rd}$ edition, 1999, and $2^{nd}$ edition, 1991. The protecting groups may be removed at a convenient subsequent stage using methods known in the art. Alternatively the interfering group may be introduced into the molecule subsequent to the reaction Step of concern.

One skilled in the art of organic synthesis will recognize that the synthesis of compounds with multiple reactive functional groups, such as —OH and $NH_2$, may require protection of certain functional groups (i.e., derivatization for the purpose of chemical compatibility with a particular reaction condition). Suitable protecting groups for the various functional groups of these compounds and methods for their installation and removal are well-known in the art of organic chemistry. A summary of many of these methods may be found in Greene & Wuts, *Protecting Groups in Organic Synthesis*, John Wiley & Sons, 3rd edition (1999).

One skilled in the art of organic synthesis will also recognize that one route for the synthesis of the Compounds of Formula (I) may be more desirable depending on the choice of appendage substituents. Additionally, one skilled in the relevant art will recognize that in some cases the order of reactions may differ from that presented herein to avoid functional group incompatibilities and thus adjust the synthetic route accordingly.

Compounds of formula vii, x, xv and xvii may be further elaborated using methods that would be well-known to those skilled in the art of organic synthesis or, for example, the methods described in the Examples below, to make the full scope of the Compounds of Formula (I).

The starting materials used and the intermediates prepared using the methods set forth in Schemes 1 and 2 may be isolated and purified if desired using conventional techniques, including but not limited to filtration, distillation, crystallization, chromatography and alike. Such materials may be characterized using conventional means, including physical constants and spectral data.

EXAMPLES

General Methods

The following examples serve only to illustrate the invention and its practice. The examples are not to be construed as limitations on the scope or spirit of the invention. In these examples, all temperatures are degrees Celsius unless otherwise noted, and "room temperature" refers to a temperature in a range of from about 20° C. to about 25° C. Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). For HPLC/MS data, the two HPLC conditions used were as follows: 1) LC2 (Waters C18 XTerra™ 3.5 μm 2.1×20 mm column with gradient 10:90-98:2 v/v CH$_3$CN/H$_2$O+v 0.05% TFA over 1.25 min then hold at 98:2 v/v CH$_3$CN/H$_2$O+v 0.05% TFA for 0.75 min; flow rate 1.5 mL/min, UV wavelength 254 nm); and 2) LC4 (Waters C18 XTerra 3.5 μm 2.1×20 mm column with gradient 10:90-98:2 v/v CH$_3$CN/H$_2$O+v 0.05% TFA over 3.25 min then hold at 98:2 v/v CH$_3$CN/H$_2$O+v 0.05% TFA for 0.75 min; flow rate 1.5 mL/min, UV wavelength 254 nm).

Mass analysis was performed with electrospray ionization in positive ion detection mode. $^1$H NMR spectra were recorded on Varian or Bruker instruments at 400-500 MHz. Concentration of solutions was carried out on a rotary evaporator under reduced pressure or by lyophilization. Flash chromatography was performed on pre-packed silica gel columns using a commercial MPLC system. Compounds described herein were synthesized as racemic mixtures unless otherwise stated in the experimental procedures.

Example 1

Preparation of Compound 1 and 2

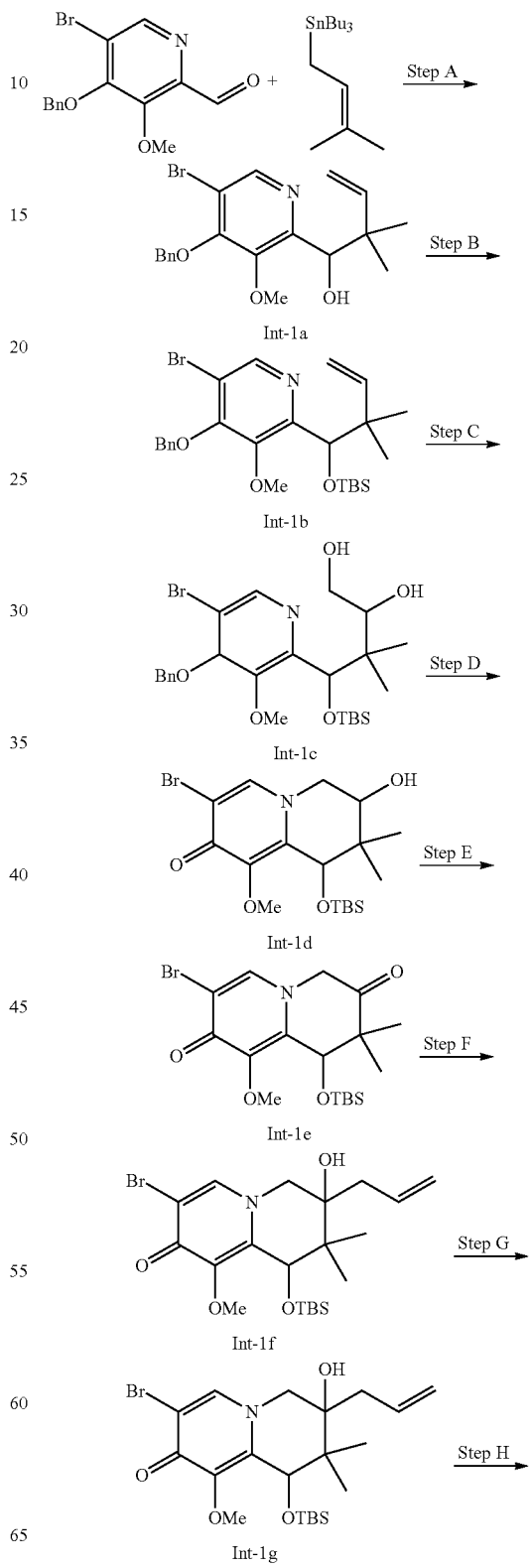

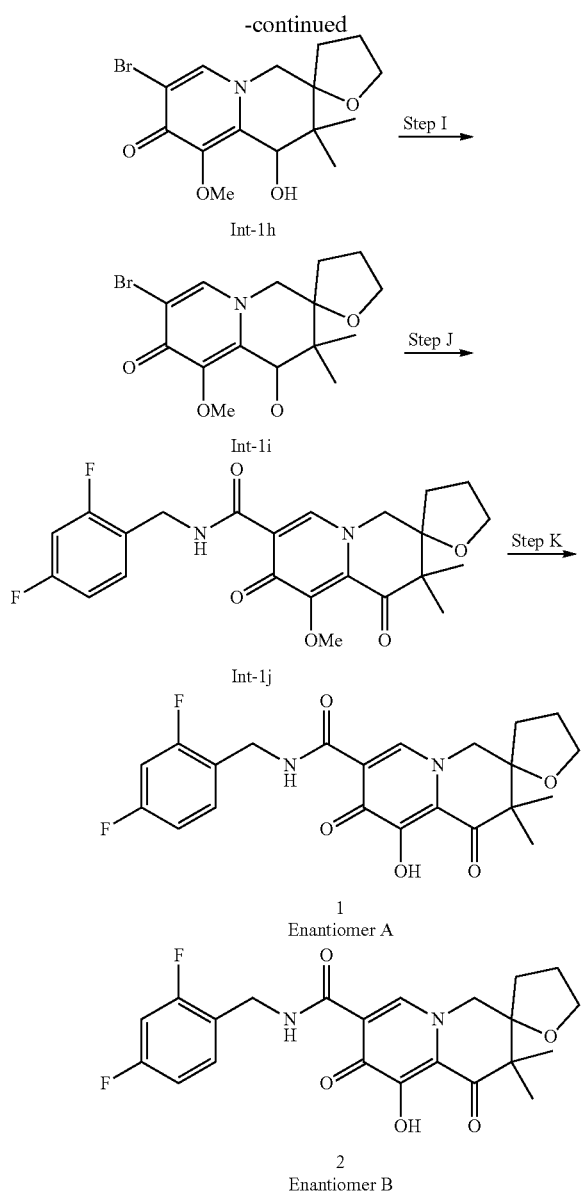

Int-1h

Int-1i

Int-1j

1
Enantiomer A

2
Enantiomer B

Step A—Synthesis of Compound Int-1a

To a solution of 4-(benzyloxy)-5-bromo-3-methoxypicolinaldehyde (4.48 g, 13.92 mmol) and tributyl(3-methylbut-2-en-1-yl)stannane (5.0 g, 13.92 mmol) in 120 mL acetonitrile at 0° C. was added stannous chloride (3.96 g, 20.88 mmol). The resulting mixture was allowed to warm to room temperature and stirred at this temperature for 15 minutes. It was diluted with 200 mL of 30% EtOAc/hexanes, and washed with 200 mL of water. The organic phase was filtered and concentrated in vacuo. The residue obtained was purified using column chromatography eluting with 15% EtOAc/hexane to provide Int-1a (3.9 g, 9.94 mmol) as an oil. LCMS anal. calcd. for $C_{19}H_{22}BrNO_3$: 391.08; Found: 392.07 (M+1)$^+$.

Step B—Synthesis of Compound Int-1b

To a solution of Int-1a (3.5 g, 8.92 mmol) in 20 mL DMF was added imidazole (1.822 g, 26.8 mmol) and tert-butyl-chlorodimethylsilane (2.69 g, 17.84 mmol). The resulting mixture was allowed to stir at 50° C. for about 15 hours. It was cooled to room temperature and diluted with 200 mL EtOAc. The reaction mixture was then washed sequentially with water and brine, dried over $Na_2SO_4$ and concentrated in vacuo. The residue obtained was purified using column chromatography eluting with 5% EtOAc/hexane to provide Int-1b (3.6 g, 7.11 mmol) as an oil. LCMS anal. calcd. for $C_{25}H_{36}BrNO_3Si$: 506.55; Found: 507.33 (M+1)$^+$.

Step C—Synthesis of Compound Int-1c

To a solution of Int-1b (4.0 g, 7.90 mmol) in 60 mL THF and 15 mL water was added 4-methylmorpholine 4-oxide (2.78 g, 23.69 mmol) and an aqueous osmium tetroxide solution (4% in water, 2.509 ml, 0.395 mmol). The resulting mixture was allowed to stir at room temperature for 24 hours, then 2.0 g sodium metabisulfite was added and the reaction was allowed to stir at room temperature for 1 hour. The resulting reaction was filtered. The filtrate was dried over $Na_2SO_4$ and concentrated in vacuo. The residue obtained was purified using column chromatography eluting with 40% EtOAc/hexane to provide Int-1c (3.8 g, 7.03 mmol) as a foam. LCMS anal. calcd. for $C_{25}H_{38}BrNO_5Si$: 540.56; Found: 542.01 (M+1)$^+$.

Step D—Synthesis of Compound Int-1d

To a stirred solution of Int-1c (4.0 g, 7.40 mmol) in 35 mL pyridine was added 4-methylbenzene-1-sulfonyl chloride (2.116 g, 11.10 mmol). The reaction mixture was allowed to stir at room temperature for 15 hours, then 5 mL MeOH was added and the resulting solution was concentrated in vacuo. The residue obtained was purified using column chromatography eluting with 70% EtOAc/hexane to provide Int-1d (2.7 g, 6.24 mmol) as a solid. LCMS anal. calcd. for $C_{18}H_{30}BrNO_4Si$: 432.43; Found: 434.12 (M+1)$^+$.

Step E—Synthesis of Compound Int-1e

To a solution of Int-1d (2.5 g, 5.78 mmol) in 50 mL DCM was added Dess-Martin periodinane (3.19 g, 7.52 mmol). The resulting mixture was allowed to stir at room temperature for 30 minutes, then was diluted with 5 mL of $H_2O$. The solid precipitate was filtered and the filtrate was concentrated in vacuo. The residue obtained was purified using column chromatography eluting with 60% EtOAc/hexane to provide Int-1e (2.0 g, 4.65 mmol) as a solid. LCMS anal. calcd. for $C_{18}H_{30}BrNO_4Si$: 430.41; Found: 432.12 (M+1)$^+$.

Step F—Synthesis of Compound Int-1f

To a stirred solution of Int-1e (1.0 g, 2.323 mmol) in 25 mL THF at 0° C. was added allylmagnesium bromide (9.3 mL, 9.29 mmol) dropwise. The resulting reaction was allowed to stir at this temperature for 30 minutes. The reaction was then quenched with 100 mL saturated $NH_4Cl$ aqueous solution and the resulting solution was extracted with 2×100 mL EtOAc. The combined extracts were dried over $Na_2SO_4$ and concentrated in vacuo. The residue obtained was purified using column chromatography eluting with 60% EtOAc/hexane to provide Int-1f (510 mg, 1.079 mmol) as a solid. LCMS anal. calcd. for $C_{21}H_{34}BrNO_4Si$: 472.49; Found: 473.96 (M+1)$^+$.

Step G—Synthesis of Compound Int-1g

To a 0° C. solution of Int-1f (450 mg, 0.952 mmol) in 10 mL THF was added borane (1 M in THF, 1.43 mL, 1.43 mmol) under $N_2$. The mixture was allowed to stir at room temperature for 1 hour. Then the following were added in succession: 2 mL water, 4.8 mL 2 N aqueous sodium hydroxide solution and hydrogen peroxide in water (1.045 g, 9.52 mmol). The resulting mixture was allowed to stir for an additional hour, then was extracted with EtOAc (3×50 mL). The combined organic extracts were washed with 20 mL brine, dried over anhydrous $MgSO_4$ and concentrated in vacuo. The residue obtained was purified using chromatography eluting with 50-100% EtOAc/hexane to provide Int- 1g (180 mg, 0.367 mmol) as a gel. LCMS anal. calcd. for $C_{21}H_{36}BrNO_5Si$: 490.50; Found: 492.10 $(M+1)^+$.

Step H—Synthesis of Compound Int-1h

The solution of Int-1g (75 mg, 0.153 mmol) in 2 mL THF was added triethylamine (30.9 mg, 0.306 mmol) and methanesulfonyl chloride (21.02 mg, 0.183 mmol). The resulting reaction was allowed to stir at this temperature for 15 minutes. It was quenched with 20 mL water. The reaction mixture was extracted with 2×30 mL EtOAc. The combined organic extracts was washed with water and brine, dried over $Na_2SO_4$ and concentrated in vacuo to provide 80 mg crude mesylated product.

The above mesylated product was added 2 mL DMF, followed by adding sodium hydride (12.23 mg, 0.306 mmol) at room temperature. The mixture was allowed to stir at room temperature for 15 minutes. It was quenched with 20 mL water. The reaction mixture was extracted with 2×30 mL EtOAc. The combined organic extracts were dried over $Na_2SO_4$ and concentrated in vacuo to provide 65 mg crude cyclized product.

The crude cyclized product was then added 2 mL THF, followed by adding 0.2 mL tetrabutylammonium fluoride (1M in THF). The resulting reaction was allowed to stir at room temperature for 30 minutes. It was concentrated in vacuo. The residue obtained was purified using Gilson HPLC eluting with 10% ACN (0.1% TFA)/$H_2O$ to 90% ACN (0.1% TFA)/$H_2O$. The desired fraction was collected and dried via lyopholization to provide Int-1h (35 mg, 0.098 mmol) as a solid. LCMS anal. calcd. for $C_{15}H_{20}BrNO_4$: 358.23; Found: 359.94 $(M+1)^+$.

Step I—Synthesis of Compound Int-1i

The solution of Int-1h (40 mg, 0.112 mmol) in 2 mL $CH_2Cl_2$ was added Dess-Martin periodinane (71.0 mg, 0.167 mmol). The mixture was allowed to stir at room temperature for 20 min and was added a drop of water. The resulting reaction was filtered and the filtrate was concentrated in vacuo. To the residue obtained was added 3 mL DMSO and purified using Gilson HPLC eluting with 10% ACN (0.1% TFA)/$H_2O$ to 90% ACN (0.1% TFA)/$H_2O$. The desired fraction was collected and dried via lyopholization to provide Int-1i (30 mg, 0.084 mmol) as a solid. LCMS anal. calcd. for $C_{15}H_{18}BrNO_4$: 356.21; Found: 357.91 $(M+1)^+$.

Step J—Synthesis of Compound Int-1j

The solution of Int-1i (30 mg, 0.084 mmol), N-ethyl-N-isopropylpropan-2-amine (32.7 mg, 0.253 mmol), (2, 4-difluorophenyl)methanamine (24.11 mg, 0.168 mmol) and (oxybis(2,1-phenylene))bis(diphenylphosphine) (4.54 mg, 8.42 µmol) in 1 mL DMSO was added diacetoxypalladium (1.891 mg, 8.42 µmol). The above mixture was then put under CO atmosphere (using a CO filled balloon) at 80° C. for 1 hour. The resulting reaction was cooled down and added 0.2 mL $H_2O$. The reaction mixture was purified directly by Gilson HPLC eluting with 10% ACN (0.1% TFA)/$H_2O$ to 90% ACN (0.1% TFA)/$H_2O$. The desired fraction was collected and dried via lyopholization to provide Int-1j (23 mg, 0.052 mmol) as a solid. LCMS anal. calcd. for $C_{23}H_{24}F_2N_2O_5$: 446.44; Found: 447.00 $(M+1)^+$.

Step K—Synthesis of Compounds 1 and 2

The compound Int-1j (23 mg, 0.052 mmol) was separated by chiral OD (30×250 nm) column eluting with 50% MeOH/$CO_2$ to provide two enantiomeric pure isomers with 9 mg each.

To a stirred solution of each isomer (9 mg, 0.020 mmol) in 1 mL DMF was added lithium chloride (17.09 mg, 0.403 mmol). The mixture was allowed to stir at 100° C. for 30 minutes. The resulting reaction was cooled down and added 0.2 mL $H_2O$. The mixture was purified directly by Gilson HPLC eluting with 10% ACN (0.1% TFA)/$H_2O$ to 90% ACN (0.1% TFA)/$H_2O$. The desired fraction was collected and dried by via lyophilization to provide 1 (6.5 mg, 0.015 mmol) and 2 (6.0 mg, 0.014 mmol) as a solid. LCMS anal. calcd. for $C_{22}H_{22}F_2N_2O_5$: 432.43; Found: 433.26 $(M+1)^+$. $^1H$ NMR (400 MHz, $CDCl_3$): δ 10.45 (broad, 1 H); 8.42 (s, 1 H); 7.36-7.41 (m, 1 H); 6.81-6.86 (m, 2 H); 4.64-4.72 (m, 2 H); 4.31 (d, J=10.8 Hz, 1 H); 3.96-4.01 (m, 2 H); 3.88-3.92 (m, 1 H); 2.15-2.20 (m, 1 H); 2.04-2.11 (m, 2 H); 1.73-1.81 (m, 1 H); 1.35 (s, 3 H); 1.31 (s, 3 H).

Example 2

Preparation of Compound 3 and 4

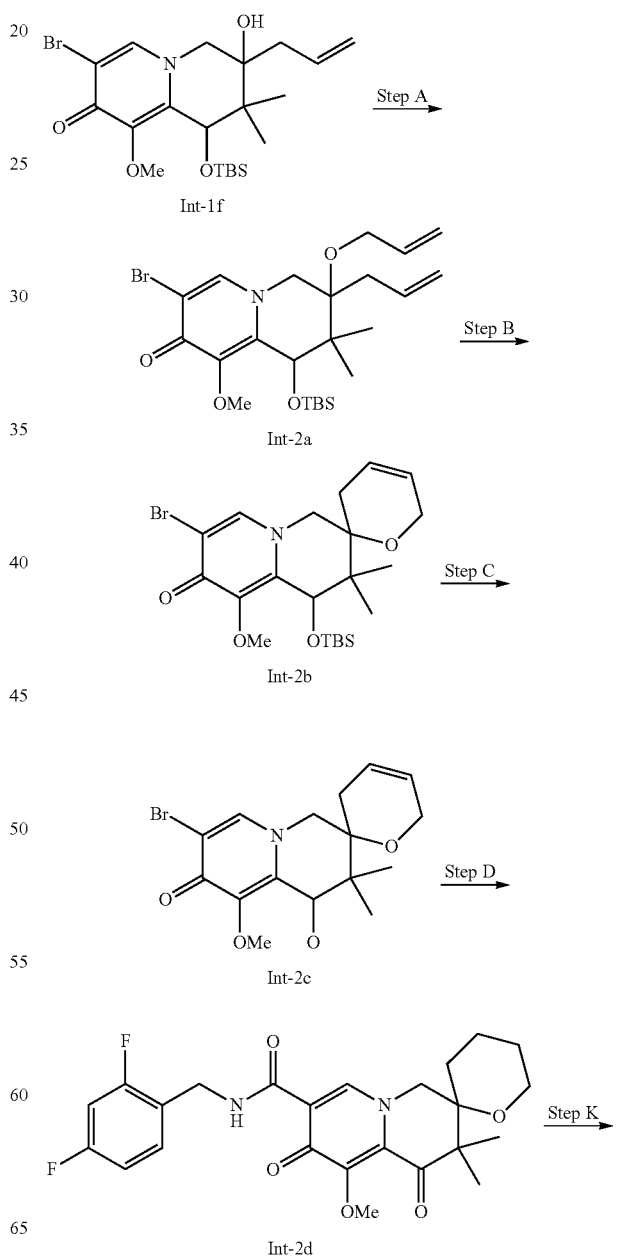

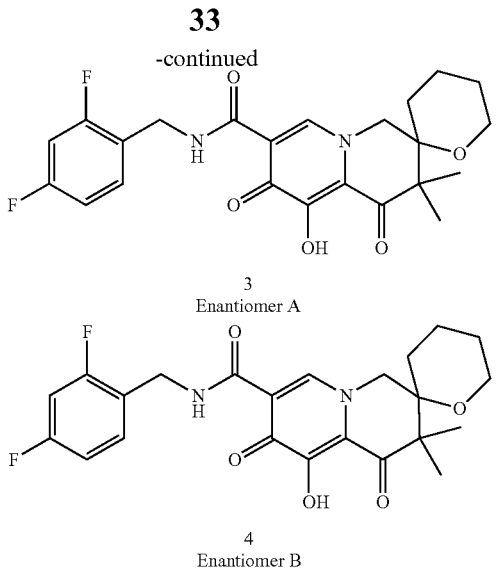

3
Enantiomer A

4
Enantiomer B

Step A—Synthesis of Compound Int-2a

The solution of Int-1f (100 mg, 0.212 mmol) in 2 mL DMF was added 3-iodoprop-1-ene (71.1 mg, 0.423 mmol), followed by adding sodium hydride (16.93 mg, 0.423 mmol) at 0° C. The resulting reaction was then allowed to stir at this temperature for 1 hour. It was quenched with a drop of water. The mixture was purified directly by Gilson HPLC, eluting with 10% ACN (0.1% TFA)/H$_2$O to 90% ACN (0.1% TFA)/H$_2$O. The desired fraction was collected and dried via lyopholization to provide Int-2a (70 mg, 0.137 mmol) as a solid. LCMS anal. calcd. for C$_{24}$H$_{38}$BrNO$_4$Si: 512.55; Found: 514.01 (M+1)$^+$.

Step B—Synthesis of Compound Int-2b

To a solution of Int-2a (70 mg, 0.137 mmol) in 2 mL CH$_2$Cl$_2$ was added Zhan catalyst-1B (15.05 mg, 0.020 mmol). The resulting reaction was allowed to stir at room temperature for 2 hours. It was concentrated in vacuo. The residue obtained was purified using column chromatography eluting with 50% EtOAc/hexane to provide Int-2b (40 mg, 0.083 mmol) as a solid. LCMS anal. calcd. for C$_{22}$H$_{34}$BrNO$_4$Si: 484.50; Found: 486.12 (M+1)$^+$.

Step C—Synthesis of Compound Int-2c

The solution of Int-2b (40 mg, 0.083 mmol) in 2 mL THF was added tetrabutylammonium fluoride (1 M in THF, 124 μl, 0.124 mmol). The resulting reaction was allowed to stir at room temperature for 30 minutes. It was concentrated in vacuo and the residue obtained was added 2 mL DMSO. The mixture was purified using Gilson HPLC eluting with 10% ACN (0.1% TFA)/H$_2$O to 90% ACN (0.1% TFA)/H$_2$O. The desired fraction was collected and dried via lyopholization to provide 22 mg alcohol intermediate.

The above alcohol intermediate was then added 2 mL DCM, followed by Dess-Martin periodinane (70.0 mg, 0.165 mmol). It was allowed to stir at room temperature for 30 minutes. It was concentrated in vacuo and the residue obtained was added 2 mL DMSO. The mixture was purified using Gilson HPLC eluting with 10% ACN (0.1% TFA)/H$_2$O to 90% ACN (0.1% TFA)/H$_2$O. The desired fraction was collected and dried via lyopholization to provide Int-2c (15 mg, 0.041 mmol) as a solid. LCMS anal. calcd. for C$_{16}$H$_{18}$BrNO$_4$: 368.22; Found: 369.94 (M+1)$^+$.

Step D—Synthesis of Compound Int-2d

The mixture of Int-2c (15 mg, 0.041 mmol), N-ethyl-N-isopropylpropan-2-amine (15.79 mg, 0.122 mmol), (2,4-difluorophenyl)methanamine (11.66 mg, 0.081 mmol) and (oxybis(2,1-phenylene))bis(diphenylphosphine) (2.194 mg, 4.07 μmol) in 1 mL DMSO was added diacetoxypalladium (0.915 mg, 4.07 μmol). The above mixture was then put under CO atmosphere (using a CO filled balloon) at 80° C. for 1 hour. The resulting reaction was cooled down and added 0.5 mL H$_2$O. The mixture was purified using Gilson HPLC eluting with 10% ACN (0.1% TFA)/H$_2$O to 90% ACN (0.1% TFA)/H$_2$O. The desired fraction was collected and dried via lyopholization to provide 12 mg intermediate.

The above 12 mg intermediate was then added 1 mL MeOH, followed by adding 2 mg 10% Pd/carbon. The mixture was allowed to stir at room temperature for 1 hour. The resulting reaction was filtered and concentrated to provide Int-2d (10 mg, 0.022 mmol) as a solid. LCMS anal. calcd. for C$_{24}$H$_{26}$F$_2$N$_2$O$_5$: 460.47; Found: 461.04 (M+1)$^+$.

Step E—Synthesis of Compounds 3 and 4

The compound Int-2d (10 mg, 0.022 mmol) was separated by chiral AS (21×250 nm) column eluting with 20% MeOH/CO$_2$ to provide two enantiomeric pure isomers with 4 mg each.

To a stirred solution of each isomer (4 mg, 0.009 mmol) in 1 mL DMF was added lithium chloride (7.37 mg, 0.174 mmol). The mixture was allowed to stir at 100° C. for 30 minutes. The resulting reaction was cooled down and added 0.2 mL H$_2$O. The mixture was purified directly by Gilson HPLC eluting with 10% ACN (0.1% TFA)/H$_2$O to 90% ACN (0.1% TFA)/H$_2$O. The desired fraction was collected and dried via lyopholization to provide 3 (3.0 mg, 0.0067 mmol) and 4 (3.0 mg, 0.0067 mmol) as a solid. LCMS anal. calcd. for C$_{23}$H$_{24}$F$_2$N$_2$O$_5$: 446.44; Found: 446.97 (M+1)$^+$. $^1$H NMR (400 MHz, CDCl$_3$): δ 10.50 (broad, 1 H); 8.47 (s, 1H); 7.37-7.42 (m, 1 H); 6.81-6.87 (m, 2 H); 4.64-4.73 (m, 3 H); 4.14 (d, J=11.2 Hz, 1 H); 3.71-3.74 (m, 1 H); 3.47-3.52 (m, 1 H); 1.74-2.08 (m, 4 H); 1.54-1.64 (m, 2 H); 1.42 (s, 3 H); 1.24 (s, 3 H).

Example 3

Preparation of Compound 5

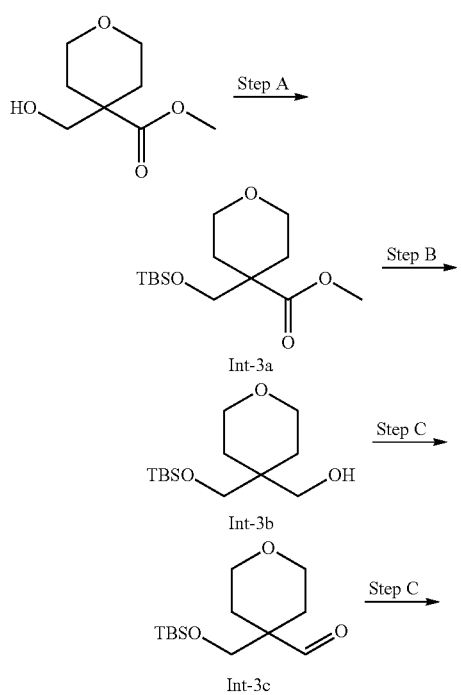

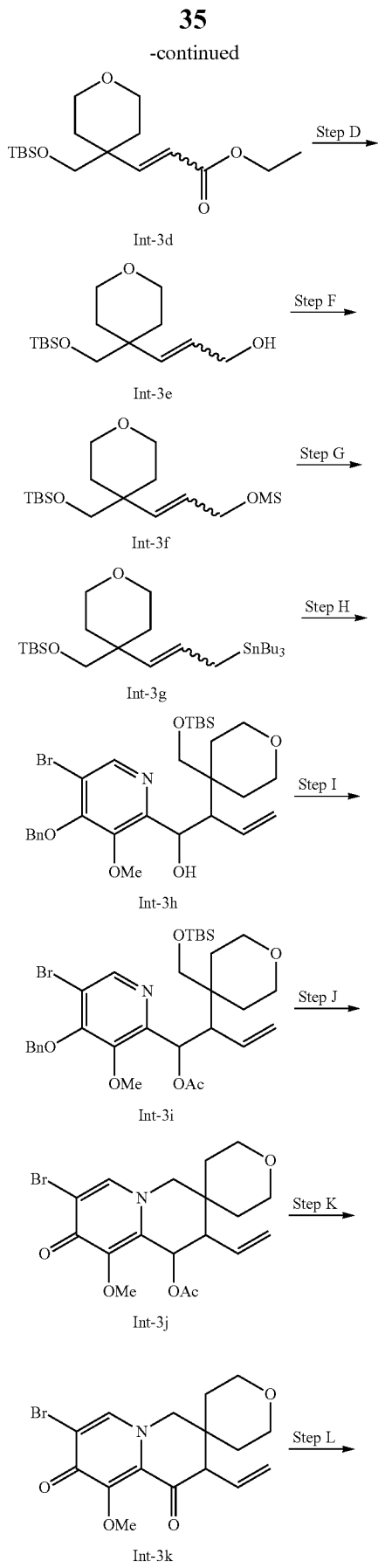

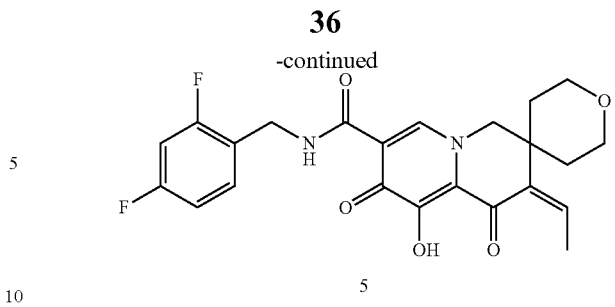

Step A—Synthesis of Compound Int-3a

The mixture of methyl 4-(hydroxymethyl)tetrahydro-2H-pyran-4-carboxylate (4.5 g, 25.8 mmol) and tert-butylchlorodimethylsilane (7.79 g, 51.7 mmol) in 50 mL DMF was added imidazole (5.28 g, 77 mmol). The resulting reaction was allowed to stir at room temperature for 12 hours. It was added 200 mL water and 200 mL EtOAc. The organic phase was separated, dried over $Na_2SO_4$ and concentrated in vacuo. The residue obtained was purified using flash chromatography eluting with 10% EtOAc/hexane to provide Int-3a (7.4 g, 25.7 mmol) as an oil. $^1$H NMR (400 MHz, $CDCl_3$): δ 3.81-3.85 (m, 2 H); 3.71 (s, 3 H); 3.59 (s, 2 H); 3.45-3.50 (m, 2 H); 2.03-2.06 (m, 2 H); 1.52-1.58 (m, 2 H); 0.91 (s, 9 H); 0.01 (s, 6 H).

Step B— Synthesis of Compound Int-3b

The solution of Int-3a (7.5 g, 26.0 mmol) in 130 mL DCM was added diisobutylaluminum hydride in toluene (57.2 ml, 57.2 mmol) dropwise at −40° C. The mixture was then slowly warmed up to 0° C. for 30 minutes. The resulting reaction was quenched with 15 mL MeOH at −40° C. To above reaction mixture was added 200 mL DCM and 200 mL Rochelle salt solution. It was allowed to stir at room temperature for 1 hour. The organic phase was separated, dried over $Na_2SO_4$ and concentrated to provide Int-3b (5.8 g, 22.27 mmol) as an oil. $^1$H NMR (400 MHz, $CDCl_3$): δ 3.61-3.70 (m, 8 H); 2.97 (broad, 1 H); 1.52-1.57 (m, 2 H); 1.42-1.47 (m, 2 H); 0.91 (s, 9 H); 0.09 (s, 6 H).

Step C— Synthesis of Compound Int-3c

A solution of Int-3b (5.8 g, 22.27 mmol) in a mixture of 16 mL DMSO and 95 mL DCM was added triethylamine (9.39 ml, 66.8 mmol) and $PySO_3$ complex (7.09 g, 44.5 mmol) at 0° C. After 10 min, the ice bath was removed and the mixture was allowed to stir at room temperature for 2 hours. It was added 200 mL $H_2O$ and 200 mL DCM. The organic phase was separated and the aqueous was extracted with 2×100 mL DCM. The combined organic was dried over $Na_2SO_4$ and concentrated in vacuo. The residue obtained was purified using column chromatography eluting with 10% EtOAc/hexane to provide Int-3c (4.0 g, 15.48 mmol) as an oil. LCMS anal. calcd. for $C_{13}H_{26}O_3Si$: 258.43; Found: 259.11 $(M+1)^+$.

Step D—Synthesis of Compound Int-3d

The solution ethyl 2-(trimethylsilyl)acetate (3.23 g, 20.12 mmol) in 150 mL THF at −78° C. was added lithium diisopropylamide (1 M in THF, 20.12 ml, 20.12 mmol) dropwise. The reaction mixture was allowed to stir for 15 minutes, and then Int-3c (4.0 g, 15.48 mmol) in 5 mL THF was added dropwise. The reaction mixture was allowed to warm up to 40° C. over 3 h, saturated aqueous $NH_4Cl$ was added (100 mL) to quench the reaction. The reaction mixture was extracted with ethyl acetate (2×150 mL) and the combined organic extracts were washed with brine (150 mL). After drying over $MgSO_4$ and filtration, the solvent was removed in vacuo. The residue obtained was purified using column chromatography eluting with 15% EtOAc/hexane to provide Int-3d (3.5 g, 10.65 mmol) as an oil. LCMS anal. calcd. for $C_{17}H_{32}O_4Si$: 328.52; Found: 329.11 (M+1)$^+$.

Step E—Synthesis of Compound Int-3e

The solution of e Int-3d (3.4 g, 10.35 mmol) in 100 mL DCM was added diisobutylaluminum hydride in toluene (22.77 ml, 22.77 mmol) dropwise at −40° C. The mixture was then slowly warmed up to 0° C. for 30 minutes. The resulting reaction was quenched with 5 mL MeOH at −40° C. To above mixture was then added 100 mL DCM and 100 mL Rochelle salt solution. It was allowed to stir at room temperature for 2 hours. The organic phase was separated, dried over $Na_2SO_4$ and concentrated to provide Int-3e (2.2 g, 7.68 mmol) as an oil. LCMS anal. calcd. for $C_{15}H_{30}O_3Si$: 286.48; Found: 287.32 (M+1)$^+$.

Step F— Synthesis of Compound Int-3f

To a solution of Int-3e (2.20 g, 7.68 mmol) in 80 mL THF was added triethylamine (2.3 g, 23.04 mmol) and methanesulfonyl chloride (1.76 g, 15.36 mmol) at 0° C. The resulting reaction was allowed to stir at 0° C. for 1 hour. It was diluted with 100 mL of EtOAc and the reaction mixture washed with 100 mL of 0.2 N HCl aqueous solution 3 times, then with 100 mL of brine. The organic was dried over $Na_2SO_4$ and concentrated to provide Int-3f (2.7 g, 7.41 mmol) as an oil. $^1$H NMR (400 MHz, $CDCl_3$): δ 5.82 (d, J=11.8 Hz, 1 H); 5.62-5.68 (m, 1 H); 4.75 (d, J=4.4 Hz, 2 H); 3.75-3.78 (m, 2 H); 3.69 (s, 2 H); 3.54-3.59 (m, 2H); 3.03 (s, 3 H); 1.69-1.75 (m, 2 H); 1.55-1.58 (m, 2 H); 0.89 (s, 9 H); 0.03 (s, 6 H).

Step G—Synthesis of Compound Int-3g

To an ice-cold solution of lithium diisopropylamide (11.3 mL, 22.63 mmol) in 70 mL THF was added tributylstannane (6.00 g, 20.57 mmol). The resulting reaction was allowed to stir at this temperature for 15 minutes. It was then cooled to −78° C., and a solution of Int-3g (2.50 g, 6.86 mmol) in 10 mL of THF was added via syringe. The resulting reaction was allowed to stir at −78° C. for 30 minutes. It was diluted with 150 mL of 20% EtOAc/hexanes, and washed 150 mL of water. The organic was dried over $Na_2SO_4$, concentrated in vacuo. The residue obtained was purified using column chromatography eluting initially with hexanes to removed $Bu_3SnH$, and then with 5% EtOAc/hexanes to provide Int-3g (1.80 g, 3.22 mmol) as an oil. $^1$H NMR (400 MHz, $CDCl_3$): δ 5.56-5.62 (m, 1 H); 5.08 (d, J=11.8 Hz, 1 H); 3.75-3.78 (m, 2 H); 3.57-3.62 (m, 2 H); 3.27 (s, 2 H); 1.77-1.86 (m, 6 H); 1.48-1.54 (m, 6 H); 1.29-1.38 (m, 9 H); 0.87-0.95 (m, 24 H); 0.04 (s, 6 H).

Step H—Synthesis of Compound Int-3h

The solution of 4-(benzyloxy)-5-bromo-3-methoxypicolinaldehyde (1.036 g, 3.22 mmol) and Int-3g (1.8 g, 3.22 mmol) in 32 mL acetonitrile at 0° C. was added stannous chloride (0.976 g, 5.15 mmol). The resulting reaction was then allowed to warm to room temperature and stirred for 30 minutes. To this, was added 100 mL of water. The resulting mixture was allowed to stir at room temperature for 30 minutes. It was diluted with 100 mL of 30% EtOAc/hexanes. The organic phase was separated and filtered. The mother liquor was concentrated in vacuo and the residue was purified using column chromatography eluting with 20% EtOAc/hexane to provide Int-3h (1.2 g, 2.025 mmol) as an oil. LCMS anal. calcd. for $C_{29}H_{42}BrNO_5Si$: 592.64; Found: 594.17 (M+1)$^+$.

Step I—Synthesis of Compound Int-3i

To a solution of Int-3h (1.0 g, 1.687 mmol) in acetic anhydride (4.0 g, 39.2 mmol) was added triethylamine (1.0 g, 9.88 mmol) and N, N-dimethylpyridin-4-amine (0.103 g, 0.844 mmol). The mixture was allowed to stir at room temperature for 1 hour. The solvent was removed under vacuum. The residue obtained was purified using column chromatography eluting with 25% EtOAc/hexanes to Int-3i (1.0 g, 1.576 mmol) as a foam. LCMS anal. calcd. for $C_{31}H_{44}BrNO_6Si$: 634.67; Found: 636.19 (M+1)$^+$.

Step J—Synthesis of Compound Int-3j

The solution of Int-3i (1.0 g, 1.576 mmol) in 10 mL DMF was added acetic acid (0.473 g, 7.88 mmol) and tetrabutylammonium fluoride in THF (3.15 ml, 3.15 mmol). The mixture was allowed to stir at room temperature for 48 hours. It was concentrated in vacuo to remove most of DMF. The residue obtained was purified using column chromatography eluting with 100% EtOAc to provide 360 mg alcohol.

The above alcohol (360 mg, 0.79 mmol) in 20 mL pyridine was added 4-methylbenzene-1-sulfonyl chloride (264 mg, 1.40 mmol). The mixture was allowed to stir at room temperature for about 15 hours, followed by heated at 80° C. for 5 hours. The resulting reaction was then added 5 mL MeOH and concentrated in vacuo to remove most of pyridine. The residue obtained was purified using column chromatography to provide Int-3j (80 mg, 0.097 mmol) as a solid. LCMS anal. calcd. for $C_{18}H_{22}BrNO_5$: 412.2; Found: 413.96 (M+1)$^+$.

Step K— Synthesis of Compound Int-3k

The solution of Int-3j (15 mg, 0.036 mmol) in 1 mL MeOH was added potassium carbonate (15.09 mg, 0.109 mmol). The mixture was allowed to stir at room temperature for 1 hour. It was concentrated in vacuo and the residue obtained was added 5 mL 10% MeOH/DCM. It was filtered and the filtrate was concentrated in vacuo to provide 20 mg crude product.

The above crude product was then added 2 mL DCM, followed by adding Dess-Martin periodinane (30.9 mg, 0.073 mmol). It was allowed to stir at room temperature for 1 hour. To this, it was added a drop of water. The mixture was loaded ontosilic-gel column directly and eluted with 6% MeOH/DCM to provide Int-3k (10 mg, 0.027 mmol) as a solid. LCMS anal. calcd. for $C_{16}H_{18}BrNO_4$: 368.22; Found: 370.01 (M+1)$^+$.

Step L—Synthesis of Compound 5

The mixture of Int-3k (18 mg, 0.049 mmol), N-ethyl-N-isopropylpropan-2-amine (18.95 mg, 0.147 mmol), (2,4-difluorophenyl)methanamine (10.50 mg, 0.073 mmol)) and (oxybis(2,1-phenylene))bis(diphenylphosphine) (5.27 mg, 9.78 μmol) in 2 mL DMSO was added palladium acetate (2.195 mg, 9.78 μmol). The above reaction was then put on CO balloon at 80° C. for 1 hour. The resulting reaction was cooled down and added 0.5 mL $H_2O$. The mixture was purified using Gilson HPLC eluting with 10% ACN (0.1% TFA)/$H_2O$ to 90% ACN (0.1% TFA)/$H_2O$. The desired fraction was collected and dried via lyopholization to provide 12 mg intermediate.

The above intermediate (10 mg, 0.022 mmol) in 1 mL DMF was added lithium chloride (18.49 mg, 0.436 mmol). The mixture was allowed to stir at 100° C. for 1 hour. It was added 0.2 mL $H_2O$. The mixture was purified using Gilson HPLC eluting with 10% ACN (0.1% TFA)/$H_2O$ to 90% ACN (0.1% TFA)/$H_2O$. The desired fraction was collected and dried via lyopholization to provide 5 (6 mg, 0.014 mmol) as a solid. LCMS anal. calcd. for $C_{23}H_{22}F_2N_2O_5$: 444.43; Found: 444.94 (M+1)$^+$. $^1$H NMR (400 MHz, $CDCl_3$): δ 10.52 (broad, 1 H); 8.55 (s, 1 H); 7.37-7.40 (m, 1 H); 6.81-6.88 (m, 2 H); 6.53-6.88 (m, 1 H); 4.69 (s, 2 H); 4.22 (s, 2 H); 3.75-3.83 (m, 4 H); 2.30 (d, J=6.0 Hz, 3 H); 1.89-1.94 (m, 2 H); 1.64-1.68 (m, 2 H).

Example 4

Preparation of Compound 6, 7, 8, 9, 10 and 11

Enantiomer A

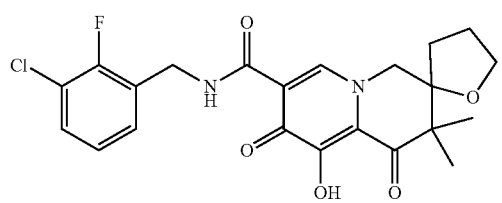

6

Enantiomer B

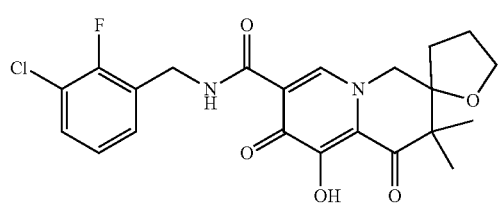

7

Enantiomer A

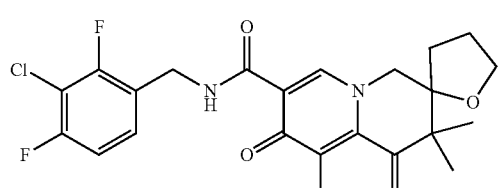

8

Enantiomer B

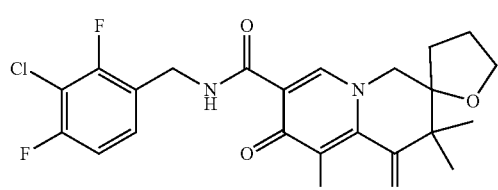

9

Enantiomer A

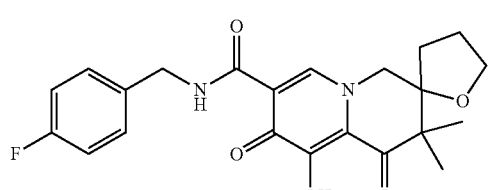

10

Enantiomer B

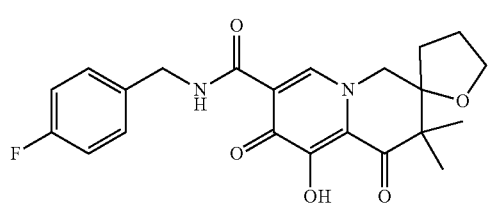

11

Starting from compound Int 1i, following essentially the same method described in Step J and Step K of example 1, only replacing (2, 4-difluorophenyl)methanamine with appropriate amine in Step J, compounds 6-11 were prepared.

Compound 6, 7: LCMS anal. calcd. for $C_{22}H_{22}ClFN_2O_5$: 448.12.43; Found: 448.86 (M+1)$^+$. $^1$H NMR (400 MHz, CDCl$_3$): δ 10.44 (broad, 1 H); 8.36 (s, 1 H); 7.26-7.30 (m, 2 H); 6.99-7.04 (m, 1 H); 4.70-4.72 (m, 2 H); 4.27 (d, J=10.8 Hz, 1 H); 3.84-4.02 (m, 3 H); 2.12-2.17 (m, 1 H); 2.03-2.06 (m, 2 H); 1.69-1.76 (m, 1 H); 1.32 (s, 3 H); 1.28 (s, 3 H).

Compound 8, 9: LCMS anal. calcd. for $C_{22}H_{22}ClF_2N_2O_5$: 466.11; Found: 466.84 (M+1)$^+$. $^1$H NMR (400 MHz, CDCl$_3$): δ 10.49 (broad, 1 H); 8.39 (s, 1 H); 7.26-7.30 (m, 1 H); 6.93 (t, J=6.8 Hz, 1 H); 4.63-4.72 (m, 2 H); 4.29 (d, J=10.8 Hz, 1 H); 3.94-4.02 (m, 2 H); 3.85-3.90 (m, 2 H); 2.13-2.18 (m, 1 H); 2.04-2.10 (m, 2 H); 1.71-1.76 (m, 1 H); 1.33 (s, 3 H); 1.29 (s, 3 H).

Compound 10, 11: LCMS anal. calcd. for $C_{22}H_{23}FN_2O_5$: 414.43; Found: 415.30 (M+1)$^+$. $^1$H NMR (400 MHz, CDCl$_3$): δ 10.51 (broad, 1 H); 8.44 (s, 1 H); 7.31-7.34 (m, 2 H); 6.99-7.03 (m, 2 H); 4.58-4.67 (m, 2 H); 4.30 (d, J=10.8 Hz, 1 H); 3.94-4.01 (m, 2 H); 3.86-3.90 (m, 1 H); 2.70 (s, 1 H); 2.13-2.18 (m, 1 H); 2.02-2.10 (m, 2 H); 1.72-1.77 (m, 1 H); 1.33 (s, 3 H); 1.30 (s, 3 H).

Example 5

Preparation of Compound 12 and 13

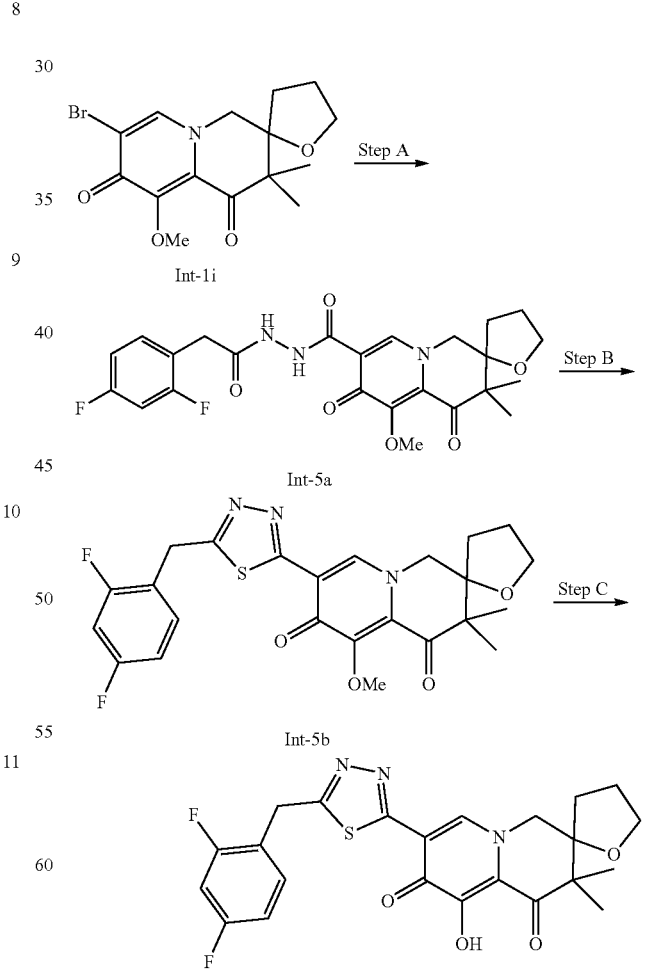

12
Enantiomer A

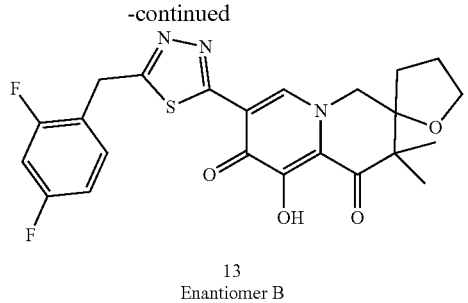

13
Enantiomer B

Example 6

Preparation of Compound Int 6a

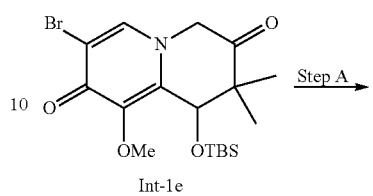

Int-1e

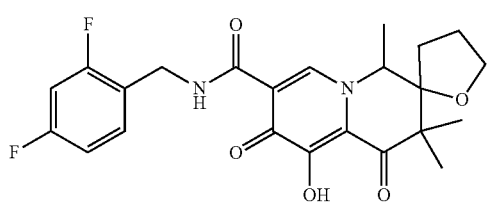

Int-6a

Step A—Synthesis of Compound Int-5a

The solution of Int-1i (40 mg, 0.112 mmol), N-ethyl-N-isopropylpropan-2-amine (43.0 mg, 0.337 mmol), (2,4-difluorophenyl)acetohydrazide (41.80 mg, 0.225 mmol) and (oxybis(2,1-phenylene))bis(diphenylphosphine) (30.2 mg, 0.056 mmol) in 2 mL DMSO was added diacetoxypalladium (12.6 mg, 0.056 mmol). The above mixture was then put under CO atmosphere (using a CO filled balloon) at 80° C. for 1 hour. The resulting reaction was cooled down and added 0.2 mL H$_2$O. The reaction mixture was purified directly by Gilson HPLC eluting with 10% ACN (0.1% TFA)/H$_2$O to 90% ACN (0.1% TFA)/H$_2$O. The desired fraction was collected and dried via lyopholization to provide Int-5a (40.0 mg, 0.082 mmol) as a solid. LCMS anal. calcd. for C$_{24}$H$_{25}$F$_2$N$_3$O$_6$: 489.17; Found: 490.20 (M+1)$^+$.

Step B—Synthesis of Compound Int-5b

The solution of Int-5a (38 mg, 0.063 mmol), Lawesson's reagent (40.5 mg, 0.100 mmol) in THF (630 µl) was allowed to stir at 60° C. for 6 hours. It was concentrated in vacuo and the residue obtained was purified using Gilson HPLC eluting with 10% ACN (0.1% TFA)/H$_2$O to 90% ACN (0.1% TFA)/H$_2$O. The desired fraction was collected and dried via lyopholization to provide Int-5b (21 mg, 0.043 mmol) as a solid. LCMS anal. calcd. for C$_{23}$H$_{21}$F$_2$N$_3$O$_4$S: 484.14; Found: 487.90 (M+1)$^+$.

Step C—Synthesis of Compounds 12 and 13

The compound Int-5b (21 mg, 0.043 mmol) was separated by chiral IA (30×250 nm) column eluting with 50% MeOH/CO$_2$ to provide two enantiomeric pure isomers with 8 mg each.

To a stirred solution of each isomer (8 mg, 0.020 mmol) in 1 mL DMF was added lithium chloride (6.96 mg, 0.164 mmol). The mixture was allowed to stir at 100° C. for 30 minutes. The resulting reaction was cooled down and added 0.2 mL H$_2$O. The mixture was purified directly by Gilson HPLC eluting with 10% ACN (0.1% TFA)/H$_2$O to 90% ACN (0.1% TFA)/H$_2$O. The desired fraction was collected and dried by via lyopholization to provide 12 (6.5 mg, 0.014 mmol) and 13 (6.5 mg, 0.014 mmol) as a solid. LCMS anal. calcd. for C$_{23}$H$_{21}$F$_2$N$_3$O$_4$S: 473.12; Found: 474.50 (M+1)$^+$.
$^1$H NMR (400 MHz, CDCl$_3$): δ 8.68 (s, 1 H); 7.29-7.34 (m, 1 H); 6.84-6.88 (m, 2 H); 4.48 (s, 2 H); 4.38 (d, J=9.0 Hz, 1 H); 4.05 (d, J=10.6 Hz, 1 H); 3.96-4.00 (m, 1 H); 3.89-3.93 (m, 1 H); 2.15-2.21 (m, 1 H); 2.03-2.13 (m, 2 H); 1.75-1.81 (m, 1 H); 1.35 (s, 3 H); 1.33 (s, 3 H).

Step A—Synthesis of Compound Int-6a

The mixture of Int-1e (500 mg, 1.162 mmol), MeI (581 µl, 9.29 mmol) and DMPU (8.6 mL) in 20 mL THF at −78° C. was added LiHMDS (2.9 mL, 2.90 mmol). The mixture was allowed to stir at −78° C. for 20 min. The resulting reaction was quenched with 40 mL saturated NH$_4$Cl aqueous solution. The reaction mixture was then extracted with 2×40 mL EtOAc. The combined extracts were washed with brine, dried over Na$_2$SO$_4$ and concentrated in vacuo. The residue obtained was purified using column chromatography to provide Int-6a (103 mg, 0.232 mmol) as a solid. LCMS anal. calcd. for C$_{19}$H$_{30}$BrNO$_4$Si: 443.11; Found: 444.10. (M+1)$^+$.

Example 7

Preparation of Compound 14 and 15

Enantiomer A

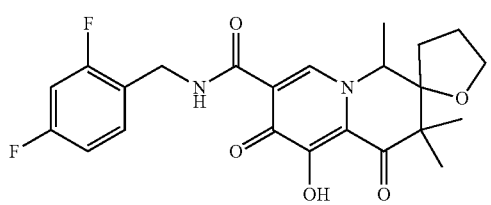

14

Enantiomer B

15

Starting from compound Int 6a and using the methods described Example 1, Step F to Step K, compounds 14 and 15 were prepared.

Compound 14 and 15: LCMS anal. calcd. for C$_{23}$H$_{24}$F$_2$N$_2$O$_5$: 446.44; Found: 447.20 (M+1)$^+$. $^1$H NMR (400 MHz, CDCl$_3$): δ 10.49 (broad, 1 H); 8.64 (s, 1 H); 7.35-7.38 (m, 1H); 6.79-6.85 (m, 2 H); 4.65 (d, J=4.4 Hz, 2 H); 4.44-4.47 (m, 1 H); 4.02-4.07 (m, 1 H); 3.94-3.99 (m, 1 H); 2.69 (s, 1 H); 2.22-2.28 (m, 1 H); 2.05-2.10 (m, 2 H); 1.89-1.95 (m, 1 H); 1.66 (d, J=5.1 Hz, 3 H); 1.31 (s, 3 H); 1.22 (s, 3 H).

Example 8

Preparation of Compound 16, 17, 18 and 19

Diastereomer A

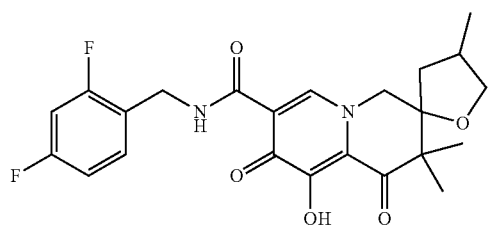
16

Diastereomer B

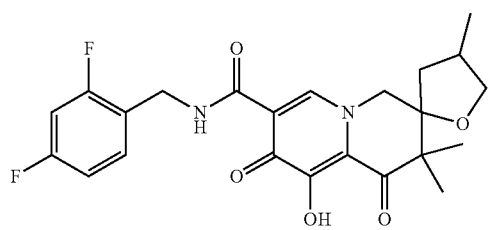
17

Diastereomer C

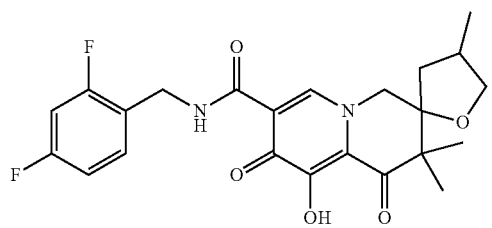
18

Diastereomer D

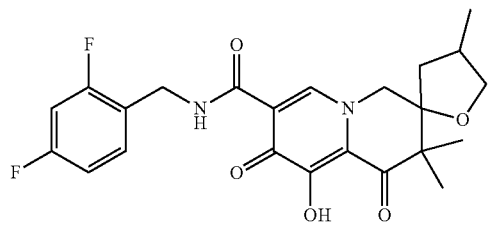
19

Starting from compound Int 1e, using the methods described in Step F to Step K of example 1, and replacing allylmagnesium bromide with the appropriate Grignard reagent in Step F, compounds 16-19 were prepared.

Compound 16: LCMS anal. calcd. for C$_{23}$H$_{24}$F$_2$N$_2$O$_5$: 446.44; Found: 447.92 (M+1)$^+$. $^1$H NMR (400 MHz, CDCl$_3$): δ 10.49 (broad, 1 H); 8.44 (s, 1 H); 7.27-7.40 (m, 1 H); 6.79-6.83 (m, 2 H); 4.65 (m, 2 H); 4.29 (d, J=10.9 Hz, 1 H); 4.06-4.10 (m, 2 H); 3.33 (m, 1 H); 2.31-2.39 (m, 3 H); 1.32 (s, 3 H); 1.27 (s, 3 H); 1.12 (d, J=4.9 Hz, 1 H).

Compound 17: LCMS anal. calcd. for C$_{23}$H$_{24}$F$_2$N$_2$O$_5$: 446.44; Found: 447.92 (M+1)$^+$. $^1$H NMR (400 MHz, CDCl$_3$): δ 10.51 (broad, 1 H); 8.44 (s, 1 H); 7.27-7.36 (m, 1 H); 6.79-6.83 (m, 2 H); 4.65 (m, 2 H); 4.30 (d, J=10.9 Hz, 1 H); 3.99-4.06 (m, 2 H); 3.40 (t, J=7.3 Hz, 1 H); 2.72 (s, 1 H); 2.49-2.57 (m, 1 H); 1.91-1.95 (m, 1 H); 1.73-1.78 (m, 1 H); 1.37 (s, 3 H); 1.27 (s, 3 H); 1.12 (d, J=4.9 Hz, 1 H).

Compound 18: LCMS anal. calcd. for C$_{23}$H$_{24}$F$_2$N$_2$O$_5$: 446.44; Found: 447.92 (M+1)$^+$. $^1$H NMR (400 MHz, CDCl$_3$): δ 10.49 (broad, 1 H); 8.44 (s, 1 H); 7.27-7.37 (m, 1 H); 6.79-6.83 (m, 2 H); 4.66 (m, 2 H); 4.29 (d, J=10.9 Hz, 1 H); 4.06-4.10 (m, 2 H); 3.33 (m, 1 H); 2.31-2.39 (m, 3 H); 1.32 (s, 3 H); 1.27 (s, 3 H); 1.11 (d, J=4.9 Hz, 1 H).

Compound 19: LCMS anal. calcd. for C$_{23}$H$_{24}$F$_2$N$_2$O$_5$: 446.44; Found: 447.92 (M+1)$^+$. $^1$H NMR (400 MHz, CDCl$_3$): δ 10.52 (broad, 1 H); 8.45 (s, 1 H); 7.33-7.44 (m, 1 H); 6.79-6.84 (m, 2 H); 4.66 (m, 2 H); 4.30 (d, J=10.9 Hz, 1 H); 4.00-4.06 (m, 2 H); 3.40 (t, J=7.3 Hz, 1 H); 2.72 (s, 1 H); 2.49-2.57 (m, 1 H); 1.91-1.95 (m, 1 H); 1.73-1.78 (m, 1 H); 1.37 (s, 3 H); 1.27 (s, 3 H); 1.12 (d, J=4.9 Hz, 1 H).

Example 9

Preparation of Compound 20, 21, 22 and 23

Diastereomer A

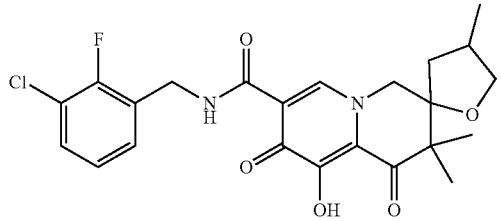
20

Diastereomer B

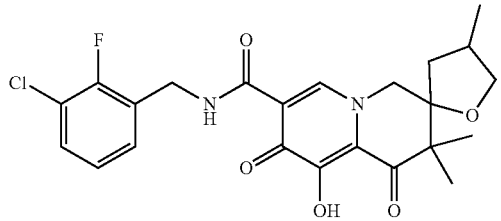
21

Diastereomer C

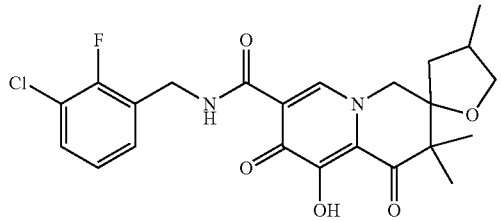
22

Diastereomer D

-continued

23

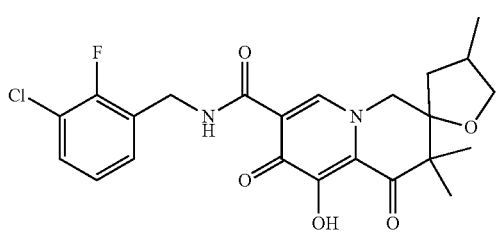

Starting from compound Int 1e, using the method described in Example 8, and replacing (2, 4-difluorophenyl)methanamine with the appropriate amine, compounds 20-23 were prepared.

Compound 20: LCMS anal. calcd. for $C_{23}H_{24}ClFN_2O_5$: 462.90; Found: 463.20 $(M+1)^+$. $^1H$ NMR (400 MHz, CDCl$_3$): δ 10.51 (broad, 1 H); 8.41 (s, 1 H); 7.27-7.31 (m, 2 H); 7.02-7.05 (m, 1 H); 4.67-4.76 (m, 2 H); 4.30 (d, J=10.6 Hz, 1 H); 4.04 (t, J=6.3 Hz, 1 H); 3.99 (d, J=10.6 Hz, 1 H); 3.38 (t, J=7.3 Hz, 1 H); 2.48-2.56 (m, 1 H); 1.92 (dd, J=6.0, 10.5 Hz, 1H); 1.76 (dd, J=8.7, 10.5 Hz, 1 H); 1.36 (s, 3 H); 1.27 (s, 3 H); 1.12 (d, J=5.1 Hz, 1 H).

Compound 21: LCMS anal. calcd. for $C_{23}H_{24}ClFN_2O_5$: 462.90; Found: 463.20 $(M+1)^+$. $^1H$ NMR (400 MHz, CDCl$_3$): δ 10.51 (broad, 1 H); 8.41 (s, 1 H); 7.27-7.31 (m, 2 H); 7.01-7.05 (m, 1 H); 4.67-4.76 (m, 2 H); 4.30 (d, J=10.6 Hz, 1 H); 4.04 (t, J=6.3 Hz, 1 H); 3.99 (d, J=10.6 Hz, 1 H); 3.38 (t, J=7.3 Hz, 1 H); 2.48-2.56 (m, 1 H); 1.92 (dd, J=6.0, 10.5 Hz, 1 H); 1.76 (dd, J=8.7, 10.5 Hz, 1 H); 1.36 (s, 3 H); 1.27 (s, 3 H); 1.12 (d, J=5.1 Hz, 1 H).

Compound 22: LCMS anal. calcd. for $C_{23}H_{24}ClFN_2O_5$: 462.90; Found: 463.20 $(M+1)^+$. $^1H$ NMR (400 MHz, CDCl$_3$): δ 10.51 (broad, 1 H); 8.41 (s, 1 H); 7.27-7.31 (m, 2 H); 7.02-7.05 (m, 1 H); 4.68-4.75 (m, 2 H); 4.30 (d, J=10.6 Hz, 1 H); 4.04 (t, J=6.3 Hz, 1 H); 3.99 (d, J=10.6 Hz, 1 H); 3.39 (t, J=7.3 Hz, 1 H); 2.48-2.56 (m, 1 H); 1.92 (dd, J=6.0, 10.5 Hz, 1H); 1.76 (dd, J=8.7, 10.5 Hz, 1 H); 1.36 (s, 3 H); 1.27 (s, 3 H); 1.12 (d, J=5.1 Hz, 1 H).

Compound 23: LCMS anal. calcd. for $C_{23}H_{24}ClFN_2O_5$: 462.90; Found: 463.20 $(M+1)^+$. $^1H$ NMR (400 MHz, CDCl$_3$): δ 10.52 (broad, 1 H); 8.42 (s, 1 H); 7.27-7.31 (m, 2 H); 7.02-7.05 (m, 1 H); 4.67-4.76 (m, 2 H); 4.30 (d, J=10.6 Hz, 1 H); 4.04 (t, J=6.3 Hz, 1 H); 3.99 (d, J=10.6 Hz, 1 H); 3.39 (t, J=7.3 Hz, 1 H); 2.48-2.56 (m, 1 H); 1.92 (dd, J=6.0, 10.5 Hz, 1 H); 1.76 (dd, J=8.7, 10.5 Hz, 1 H); 1.36 (s, 3 H); 1.27 (s, 3 H); 1.12 (d, J=5.1 Hz, 1 H).

Example 10

Preparation of Compound 24 and 25

Diastereomer A

24

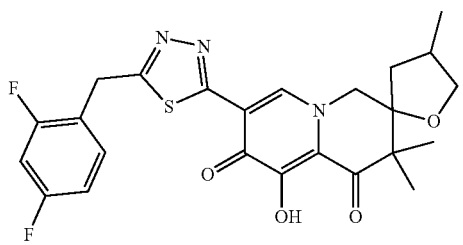

Diastereomer B

25

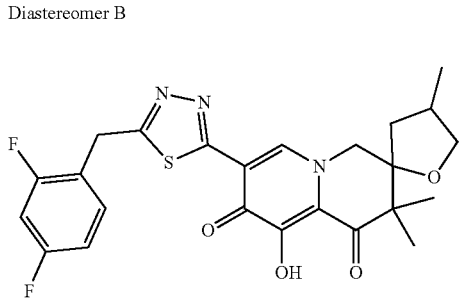

Using the methods described in Step A to Step C of Example 5, and replacing Int. 1i with the appropriate bromide in Step A, compounds 24 and 25 were prepared.

Compound 24: LCMS anal. calcd. for $C_{24}H_{23}F_2N_3O_4S$: 487.52; Found: 487.90 $(M+1)^+$. $^1H$ NMR (400 MHz, CDCl$_3$): δ 8.68 (s, 1 H); 7.27-7.32 (m, 1 H); 6.84-6.88 (m, 2 H); 4.48 (s, 2 H); 4.41 (d, J=10.6 Hz, 1 H); 4.05-4.07 (m, 2 H); 3.40 (t, J=7.8 Hz, 1 H); 2.71 (s, 1 H); 2.51-2.59 (m, 1 H); 1.96 (dd, J=6.1, 10.5 Hz, 1 H); 1.77 (dd, J=8.7, 10.5 Hz, 1 H); 1.37 (s, 3 H); 1.31 (s, 3 H); 1.14 (d, J=5.1 Hz, 1 H).

Compound 25: LCMS anal. calcd. for $C_{24}H_{23}F_2N_3O_4S$: 487.52; Found: 487.90 $(M+1)^+$. $^1H$ NMR (400 MHz, CDCl$_3$): δ 8.73 (s, 1 H); 7.27-7.32 (m, 1 H); 6.84-6.88 (m, 2 H); 4.48 (s, 2 H); 4.41 (d, J=10.6 Hz, 1 H); 4.05-4.07 (m, 2 H); 3.40 (t, J=7.8 Hz, 1 H); 2.71 (s, 1 H); 2.51-2.59 (m, 1 H); 1.96 (dd, J=6.1, 10.5 Hz, 1 H); 1.77 (dd, J=8.7, 10.5 Hz, 1 H); 1.37 (s, 3 H); 1.31 (s, 3 H); 1.14 (d, J=5.1 Hz, 1 H).

Example 11

Assay for Inhibition of HIV Replication

This assay is a kinetic assay that employs a reporter cell line (MT4-gag-GFP) to quantify the number of new cells infected in each round of replication.

MT4-GFP cells (250,000 cells/ml) were bulk-infected with HIV-1 (NL4-3 strain) at low multiplicity of infection (MOI) in RPMI+10% FBS for 24 hours. Cells were then washed once in RPMI+10% FBS and resuspended in RPMI+0% or 10% or 100% normal human serum (NHS). Test compounds were serial-diluted in DMSO on ECHO. The infected MT4-GFP cells were added to a 384-well poly-D-lysine coated black plate with clear bottom in which the diluted test compounds were placed. The cells were seeded at 8,000 cells per well and the final DMSO concentration was 0.4%. The infected cells (Green GFP cells) were quantified at both 24 and 48 hours post incubation using Acumen eX3. Viral reproductive ratio ($R_0$) was determined using the number of infected cells at 48 hours divided by the number of infected cells at 24 hours. Percent viral growth inhibition was calculated by $[1-(R-R_{tripledrug})/(R_{DMSO}-R_{tripledrug})]*100$. Compound potency IP or $IC_{50}$ was determined by a 4-parameter dose response curve analysis.

Illustrative compounds of the present invention were tested using this assay protocol and results are presented in the Table below.

| Compound No. | WILD TYPE CELL ASSAY Viking IP (0% NHS) (nM) | WILD TYPE CELL ASSAY Viking IP (100% NHS) (nM) |
|---|---|---|
| 1 | 0.9 | 175 |
| 2 | 1.2 | 2302 |
| 3 | 4.2 | 2535 |
| 4 | 6.3 | 4090 |
| 5 | 3.9 | 592 |
| 6 | 1.8 | 581 |
| 7 | 1.8 | >8000 |
| 8 | 1.7 | 585 |
| 9 | 1.7 | 6671 |
| 10 | 7.0 | 425 |
| 11 | 7.8 | 4920 |
| 12 | 5.0 | >8000 |
| 13 | 5.4 | 585 |
| 14 | 2.0 | 3296 |
| 15 | 2.4 | 149 |
| 16 | 3.1 | 634 |
| 17 | 3.1 | 307 |
| 18 | 2.7 | 855 |
| 19 | 2.6 | 453 |
| 20 | 2.0 | 1163 |
| 21 | 1.3 | 226 |
| 22 | 0.8 | 1542 |
| 23 | 1.0 | 717 |
| 24 | 2.9 | 354 |
| 25 | 3.8 | 1121 |

Treatment or Prevention of HIV Infection

The Spirocyclic Quinolizine Derivatives are useful in the inhibition of HIV, the inhibition of HIV integrase, the treatment of HIV infection and/or reduction of the likelihood or severity of symptoms of HIV infection and the inhibition of HIV viral replication and/or HIV viral production in a cell-based system. For example, the Spirocyclic Quinolizine Derivatives are useful in treating infection by HIV after suspected past exposure to HIV by such means as blood transfusion, exchange of body fluids, bites, accidental needle stick, or exposure to subject blood during surgery or other medical procedures.

Accordingly, in one embodiment, the invention provides methods for treating HIV infection in a subject, the methods comprising administering to the subject an effective amount of at least one Spirocyclic Quinolizine Derivative or a pharmaceutically acceptable salt or prodrug thereof. In a specific embodiment, the amount administered is effective to treat or prevent infection by HIV in the subject. In another specific embodiment, the amount administered is effective to inhibit HIV viral replication and/or viral production in the subject. In one embodiment, the HIV infection has progressed to AIDS.

The Spirocyclic Quinolizine Derivatives are also useful in the preparation and execution of screening assays for antiviral compounds. For example the Spirocyclic Quinolizine Derivatives are useful for identifying resistant HIV cell lines harboring mutations, which are excellent screening tools for more powerful antiviral compounds. Furthermore, the Spirocyclic Quinolizine Derivatives are useful in establishing or determining the binding site of other antivirals to the HIV Integrase.

The compositions and combinations of the present invention may be useful for treating a subject suffering from infection related to any HIV genotype.

Combination Therapy

In another embodiment, the present methods for treating or preventing HIV infection can further comprise the administration of one or more additional therapeutic agents which are not Spirocyclic Quinolizine Derivatives.

In one embodiment, the additional therapeutic agent is an antiviral agent.

In another embodiment, the additional therapeutic agent is an immunomodulatory agent, such as an immunosuppressive agent.

Accordingly, in one embodiment, the present invention provides methods for treating a viral infection in a subject, the method comprising administering to the subject: (i) at least one Spirocyclic Quinolizine Derivative (which may include two or more different Spirocyclic Quinolizine Derivatives), or a pharmaceutically acceptable salt or prodrug thereof, and (ii) at least one additional therapeutic agent that is other than a Spirocyclic Quinolizine Derivative, wherein the amounts administered are together effective to treat or prevent a viral infection.

When administering a combination therapy of the invention to a subject, therapeutic agents in the combination, or a pharmaceutical composition or compositions comprising therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a Spirocyclic Quinolizine Derivative and an additional therapeutic agent may be present in fixed amounts (dosage amounts) in a single dosage unit (e.g., a capsule, a tablet and the like).

In one embodiment, at least one Spirocyclic Quinolizine Derivative is administered during a time when the additional therapeutic agent(s) exert their prophylactic or therapeutic effect, or vice versa.

In another embodiment, at least one Spirocyclic Quinolizine Derivative and the additional therapeutic agent(s) are administered in doses commonly employed when such agents are used as monotherapy for treating a viral infection.

In another embodiment, at least one Spirocyclic Quinolizine Derivative and the additional therapeutic agent(s) are administered in doses lower than the doses commonly employed when such agents are used as monotherapy for treating a viral infection.

In still another embodiment, at least one Spirocyclic Quinolizine Derivative and the additional therapeutic agent(s) act synergistically and are administered in doses lower than the doses commonly employed when such agents are used as monotherapy for treating a viral infection.

In one embodiment, at least one Spirocyclic Quinolizine Derivative and the additional therapeutic agent(s) are present in the same composition. In one embodiment, this composition is suitable for oral administration. In another embodiment, this composition is suitable for intravenous administration. In another embodiment, this composition is suitable for subcutaneous administration. In still another embodiment, this composition is suitable for parenteral administration.

Viral infections and virus-related disorders that may be treated or prevented using the combination therapy methods of the present invention include, but are not limited to, those listed above.

In one embodiment, the viral infection is HIV infection.

In another embodiment, the viral infection is HIV infection that has progressed to AIDS.

The at least one Spirocyclic Quinolizine Derivative and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of therapy without reducing the efficacy of therapy.

In one embodiment, the administration of at least one Spirocyclic Quinolizine Derivative and the additional therapeutic agent(s) may inhibit the resistance of a viral infection to these agents.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
| --- | --- |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| dolutegravir, Tivicay ® | II |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| GSK-744 | II |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| rilpivirine, TMC-278 | nnRTI |
| ritonavir, Norvir ® | PI |
| saquinavir, Invirase ®, Fortovase ® | PI |

TABLE A-continued

| Name | Type |
| --- | --- |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor;
FI = fusion inhibitor;
PI = protease inhibitor;
nRTI = nucleoside reverse transcriptase inhibitor;
II = integrase inhibitor;
nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

In one embodiment, one or more anti-HIV drugs are selected from, lamivudine, abacavir, ritonavir, darunavir, atazanavir, emtricitabine, tenofovir, rilpivirine and lopinavir.

In another embodiment, the compound of formula (I) is used in combination with lamivudine.

In still another embodiment, the compound of formula (I) is used in combination atazanavir.

In another embodiment, the compound of formula (I) is used in combination with darunavir.

In another embodiment, the compound of formula (I) is used in combination with rilpivirine.

In one embodiment, the compound of formula (I) is used in combination with lamivudine and abacavir.

In another embodiment, the compound of formula (I) is used in combination with emtricitabine and tenofovir.

In another embodiment, the compound of formula (I) is used in combination with ritonavir and lopinavir.

In one embodiment, the compound of formula (I) is used in combination with abacavir and lamivudine.

In another embodiment, the compound of formula (I) is used in combination with lopinavir and ritonavir.

In one embodiment, the present invention provides pharmaceutical compositions comprising (i) a compound of formula (I) or a pharmaceutically acceptable salt or prodrug thereof; (ii) a pharmaceutically acceptable carrier; and (iii) one or more additional anti-HIV agents selected from lamivudine, abacavir, ritonavir and lopinavir, or a pharmaceutically acceptable salt or prodrug thereof, wherein the amounts present of components (i) and (iii) are together effective for the treatment or prophylaxis of infection by HIV or for the treatment, prophylaxis, or delay in the onset or progression of AIDS in the subject in need thereof.

In another embodiment, the present invention provides a method for the treatment or prophylaxis of infection by HIV or for the treatment, prophylaxis, or delay in the onset or progression of AIDS in a subject in need thereof, which comprises administering to the subject (i) a compound of formula (I) or a pharmaceutically acceptable salt or prodrug thereof and (ii) one or more additional anti-HIV agents selected from lamivudine, abacavir, ritonavir and lopinavir, or a pharmaceutically acceptable salt or prodrug thereof, wherein the amounts administered of components (i) and (ii) are together effective for the treatment or prophylaxis of infection by HIV or for the treatment, prophylaxis, or delay in the onset or progression of AIDS in the subject in need thereof.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57th edition (2003), the 58th edition (2004), the 59th edition (2005), and the like. The dosage ranges for a compound of the invention in these combinations are the same as those set forth above.

The doses and dosage regimen of the other agents used in the combination therapies of the present invention for the treatment or prevention of HIV infection may be determined by the attending clinician, taking into consideration the approved doses and dosage regimen in the package insert; the age, sex and general health of the subject; and the type and severity of the viral infection or related disease or disorder. When administered in combination, the Spirocyclic Quinolizine Derivative(s) and the other agent(s) may be administered simultaneously (i.e., in the same composition or in separate compositions one right after the other) or sequentially. This is particularly useful when the components of the combination are given on different dosing schedules, e.g., one component is administered once daily and another component is administered every six hours, or when the pharmaceutical compositions are different, e.g., one is a tablet and one is a capsule. A kit comprising the separate dosage forms is therefore advantageous.

Compositions and Administration

When administered to a subject, the Spirocyclic Quinolizine Derivatives may be administered as a component of a composition that comprises a pharmaceutically acceptable carrier or vehicle. The present invention provides pharmaceutical compositions comprising an effective amount of at least one Spirocyclic Quinolizine Derivative and a pharmaceutically acceptable carrier. In the pharmaceutical compositions and methods of the present invention, the active ingredients will typically be administered in admixture with suitable carrier materials suitably selected with respect to the intended form of administration, i.e., oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Solid form preparations include powders, tablets, dispersible granules, capsules, cachets and suppositories. Powders and tablets may be comprised of from about 0.5 to about 95 percent inventive composition. Tablets, powders, cachets and capsules may be used as solid dosage forms suitable for oral administration.

Moreover, when desired or needed, suitable binders, lubricants, disintegrating agents and coloring agents may also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum, and the like. Sweetening and flavoring agents and preservatives may also be included where appropriate.

Liquid form preparations include solutions, suspensions and emulsions and may include water or water-propylene glycol solutions for parenteral injection.

Liquid form preparations may also include solutions for intranasal administration.

Also included are solid form preparations which are intended to be converted, shortly before use, to liquid form preparations for either oral or parenteral administration. Such liquid forms include solutions, suspensions and emulsions.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Additionally, the compositions of the present invention may be formulated in sustained release form to provide the rate controlled release of any one or more of the components or active ingredients to optimize therapeutic effects, i.e., antiviral activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

In one embodiment, the one or more Spirocyclic Quinolizine Derivatives are administered orally.

In another embodiment, the one or more Spirocyclic Quinolizine Derivatives are administered intravenously.

In one embodiment, a pharmaceutical preparation comprising at least one Spirocyclic Quinolizine Derivative is in unit dosage form. In such form, the preparation is subdivided into unit doses containing effective amounts of the active components.

Compositions may be prepared according to conventional mixing, granulating or coating methods, respectively, and the present compositions can contain, in one embodiment, from about 0.1% to about 99% of the Spirocyclic Quinolizine Derivative(s) by weight or volume. In various embodiments, the present compositions can contain, in one embodiment, from about 1% to about 70% or from about 5% to about 60% of the Spirocyclic Quinolizine Derivative(s) by weight or volume.

The compounds of Formula I may be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions may be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the subject to be treated. The specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

For convenience, the total daily dosage may be divided and administered in portions during the day if desired. In one embodiment, the daily dosage is administered in one portion. In another embodiment, the total daily dosage is administered in two divided doses over a 24 hour period. In another embodiment, the total daily dosage is administered in three divided doses over a 24 hour period. In still another embodiment, the total daily dosage is administered in four divided doses over a 24 hour period.

The unit dosages of the Spirocyclic Quinolizine Derivatives may be administered at varying frequencies. In one embodiment, a unit dosage of a Spirocyclic Quinolizine Derivative may be administered once daily. In another embodiment, a unit dosage of a Spirocyclic Quinolizine Derivative may be administered twice weekly. In another embodiment, a unit dosage of a Spirocyclic Quinolizine Derivative may be administered once weekly. In still another embodiment, a unit dosage of a Spirocyclic Quinolizine Derivative may be administered once biweekly. In another embodiment, a unit dosage of a Spirocyclic Quinolizine Derivative may be administered once monthly. In yet another embodiment, a unit dosage of a Spirocyclic Quinolizine Derivative may be administered once bimonthly. In another embodiment, a unit dosage of a Spirocyclic Quinolizine Derivative may be administered once every 3 months. In a further embodiment, a unit dosage of a Spirocyclic Quinolizine Derivative may be administered once every 6 months. In another embodiment, a unit dosage of a Spirocyclic Quinolizine Derivative may be administered once yearly.

The amount and frequency of administration of the Spirocyclic Quinolizine Derivatives will be regulated according to the judgment of the attending clinician considering such factors as age, condition and size of the subject as well as severity of the symptoms being treated. The compositions of the invention can further comprise one or more additional therapeutic agents, selected from those listed above herein.

Kits

In one aspect, the present invention provides a kit comprising a therapeutically effective amount of at least one Spirocyclic Quinolizine Derivative, or a pharmaceutically acceptable salt or prodrug of said compound and a pharmaceutically acceptable carrier, vehicle or diluent.

In another aspect the present invention provides a kit comprising an amount of at least one Spirocyclic Quinolizine Derivative, or a pharmaceutically acceptable salt or prodrug of said compound and an amount of at least one additional therapeutic agent listed above, wherein the amounts of the two or more active ingredients result in a desired therapeutic effect. In one embodiment, the one or more Spirocyclic Quinolizine Derivatives and the one or more additional therapeutic agents are provided in the same container. In one embodiment, the one or more Spirocyclic Quinolizine Derivatives and the one or more additional therapeutic agents are provided in separate containers.

The present invention is not to be limited by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference.

What is claimed is:
1. A compound having the formula (I):

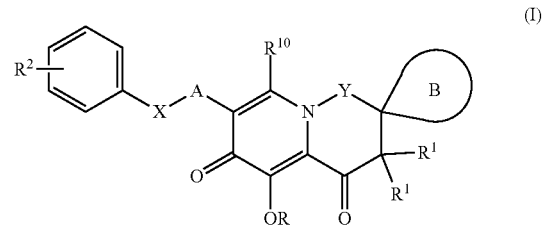

or a pharmaceutically acceptable salt or prodrug thereof, wherein:
A is —NHC(O)— or 5 or 6-membered monocyclic heteroaryl;
B is 3 to 8-membered monocyclic heterocycloalkyl, which may be optionally substituted with one or more groups, each independently selected from $R^6$;
X is $C_1$-$C_3$ alkylene;
Y is —$CH_2$—, —$CH(R^6)$— or —$N(R^3)$—;
R is H or benzyl;
each occurrence of $R^1$ is independently selected from H, $C_1$-$C_6$ alkyl, $C_1$-$C_6$ haloalkyl, $C_2$-$C_6$ alkenyl, —($C_1$-$C_6$ alkylene)—O—($C_1$-$C_6$ alkyl), —($C_1$-$C_6$ alkylene)$_m$-Z—($C_1$-$C_3$ alkylene)$_m$-$R^{11}$, —$N(R^{11})_2$ and —$OR^7$, or both $R^1$ groups and the common carbon atom to which they are attached, join to form an exocyclic olefin group having the formula:

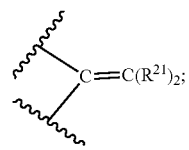

$R^2$ represents up to 3 optional substituents, each independently selected from halo, $C_1$-$C_6$ alkyl, —O—($C_1$-$C_6$ alkyl) and $C_1$-$C_6$ haloalkyl;
$R^3$ is selected from H, $C_1$-$C_6$ alkyl, —$SO_2R^4$, —$C(O)R^4$, —( $C_1$-$C_6$ alkylene)$_m$-$C(O)N(R^5)_2$, —($C_2$-$C_4$ alkylene)-O—($C_1$-$C_6$ alkyl), —($C_2$-$C_4$ alkylene)-S—($C_1$-$C_6$ alkyl), —($C_2$-$C_4$ alkylene)-$SO_2$—($C_1$-$C_6$ alkyl), —($C_2$-$C_4$ alkylene)-N—($C_1$-$C_6$ alkyl)$_2$, —($C_1$-$C_6$ alkylene)-Z—($C_1$-$C_3$ alkylene)$_m$-$R^{11}$, $C_3$-$C_7$ cycloalkyl, phenyl, 4 to 8-membered monocyclic heterocycloalkyl, 6-membered monocyclic heteroaryl and 8 to 10-membered bicyclic heteroaryl;
each occurrence of $R^4$ is independently selected from H, $C_1$-$C_6$ alkyl, $C_1$-$C_6$ haloalkyl, $C_3$-$C_7$ cycloalkyl, phenyl, 3 to 8-membered monocyclic heterocycloalkyl, 6-membered monocyclic heteroaryl and 8 to 10-membered bicyclic heteroaryl, wherein said $C_3$-$C_7$ cycloalkyl group, said phenyl group, said 3 to 8-membered monocyclic heteroaryl group, said 6-membered monocyclic heteroaryl group and said 8 to 10-membered bicyclic heteroaryl group may be optionally substituted with one or more groups, each independently selected from $R^6$;
each occurrence of $R^5$ is independently selected from H, $C_1$-$C_6$ alkyl, $C_3$-$C_7$ cycloalkyl, —($C_1$-$C_6$ alkylene)-N($R^7$)$_2$, $C_1$-$C_6$ haloalkyl, —C(O)O($C_1$-$C_6$ alkyl), —($C_1$-

$C_6$ alkylene)$_m$-Z—($C_1$-$C_3$ alkylene)$_m$-$R^{11}$, —($C_1$-$C_6$ alkylene)$_m$-$R^8$ and —($C_1$-$C_6$ alkylene)-O—($C_1$-$C_6$ alkyl);

each occurrence of $R^6$ is independently selected from halo, $C_1$-$C_6$ alkyl, $C_1$-$C_6$ haloalkyl, —($C_1$-$C_6$ alkylene)$_m$-Z—($C_1$-$C_3$ alkylene)$_m$-$R^{11}$, —N($R^{20}$)$_2$, 3 to 8-membered monocyclic heterocycloalkyl, 6 to 10-membered bicyclic heterocycloalkyl, —O—($C_1$-$C_6$ alkyl), —O—($C_6$-$C_{10}$ aryl), —O—($C_1$-$C_6$ alkylene)—O—($C_1$-$C_6$ alkyl), —O—($C_1$-$C_6$ haloalkyl), —O—($C_1$-$C_6$ alkylene)-O—($C_1$-$C_6$ alkylene)-O—($C_1$-$C_6$ alkyl), —S(O)$_2$($C_1$-$C_6$ alkyl), —NHS(O)$_2$-($C_1$-$C_6$ alkyl), —S(O)$_2$NH—($C_1$-$C_6$ alkyl), —OC(O)—($C_1$-$C_6$ haloalkyl), —($C_1$-$C_6$ alkylene)$_m$—C(O)O—($C_1$-$C_6$ alkyl), —($C_1$-$C_6$ alkylene)$_m$-C(O)—($C_1$-$C_6$ alkyl), —($C_1$-$C_6$ alkylene)$_m$-C(O)N($R^7$)$_2$, $C_1$-$C_6$ hydroxyalkyl, —P(O)(O$R^9$)$_2$ and —CN;

each occurrence of $R^7$ is independently selected from H, $C_1$-$C_6$ alkyl, $C_3$-$C_7$ cycloalkyl, $C_1$-$C_6$ haloalkyl, —C(O)O($C_1$-$C_6$ alkyl), —($C_1$-$C_6$ alkylene)$_m$-Z—($C_1$-$C_3$ alkylene)$_m$-$R^{11}$, —($C_1$-$C_6$ alkylene)$_m$-$R^8$ and -($C_1$-$C_6$ alkylene)—O—($C_1$-$C_6$ alkyl);

each occurrence of $R^8$ is independently selected from H, $C_1$-$C_6$ alkyl, $C_3$-$C_7$ cycloalkyl, 5 or 6-membered monocyclic heteroaryl and 3 to 8-membered monocyclic heterocycloalkyl;

each occurrence of $R^9$ is independently selected from H, $C_1$-$C_6$ alkyl and —($C_1$-$C_6$ alkylene)$_m$-Z—($C_1$-$C_3$ alkylene)$_m$-$R^{11}$;

$R^{10}$ is selected from H, $C_1$-$C_6$ alkyl, $C_3$-$C_7$ cycloalkyl and —($C_1$-$C_4$ alkylene)-O—($C_1$-$C_6$ alkyl);

each occurrence of $R^{11}$ is independently selected from —P(O)(—O$R^{18}$)$_2$,

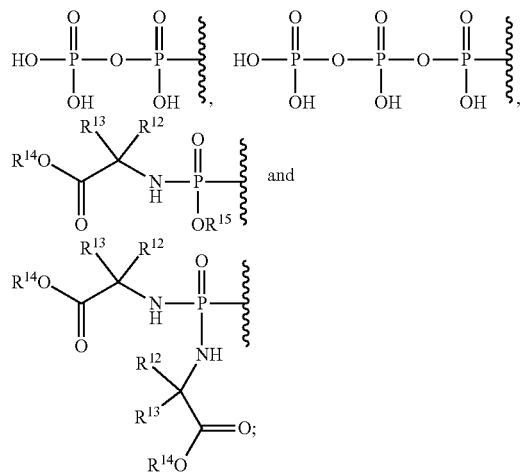

each occurrence of $R^{12}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —O$R^{16}$, —S$R^{16}$, guanidino, —N($R^{16}$)$_2$, —C(O)O$R^{16}$, —C(O)N($R^{16}$)$_2$, —NHC(O)$R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —O$R^{16}$;

each occurrence of $R^{13}$ is independently selected from H, $C_1$-$C_6$ alkyl, $C_3$-$C_7$ cycloalkyl, phenyl or benzyl, wherein said $C_1$-$C_6$ alkyl may be optionally substituted with a group selected from halo, —O$R^{16}$, —S$R^{16}$, guanidino, —N($R^{16}$)$_2$, —C(O)O$R^{16}$, —C(O)N($R^{16}$)$_2$, —NHC(O)$R^{16}$, 5- or 6-membered monocyclic heteroaryl and 9- or 10-membered bicyclic heteroaryl, and wherein said phenyl group and said benzyl group may be optionally substituted with up to 2 groups, each independently selected from $C_1$-$C_6$ alkyl, halo and —O$R^{16}$;

each occurrence of $R^{14}$ is independently selected from H, $C_1$-$C_{20}$ alkyl, $C_2$-$C_{20}$ alkenyl, —($C_1$-$C_3$ alkylene)$_m$-($C_3$-$C_7$ cycloalkyl), —($C_1$-$C_3$ alkylene)$_m$-($C_6$-$C_{10}$ aryl) or —($C_1$-$C_3$ alkylene)$_m$-adamantyl, wherein said $C_1$-$C_{20}$ alkyl group, said $C_2$-$C_{20}$ alkenyl group, said $C_6$-$C_{10}$ aryl group and said adamantyl group may be optionally substituted with up to three groups, each independently selected from halo, —O$R^{16}$, —C(O)O$R^{16}$, CN, NO$_2$, $C_1$-$C_6$ haloalkyl, $C_1$-$C_6$ hydroxyalkyl, $C_3$-$C_7$ cycloalkyl, $C_6$-$C_{10}$ aryl, 5- or 6-membered monocyclic heteroaryl, 9- or 10-membered bicyclic heteroaryl, —N($R^{16}$)$_2$, —C(O)N($R^{16}$)$_2$ —S$R^{16}$, —S(O)$R^{16}$, —S(O)$_2R^{16}$, —S(O)$_2$N($R^{16}$)$_2$, —NHC(O)$R^{16}$, —NHC(O)O$R^{16}$ and —NHC(O)N($R^{16}$)$_2$;

$R^{15}$ is selected from H, $C_6$-$C_{10}$ aryl, 5- or 6-membered monocyclic heteroaryl and 9- or 10-membered bicyclic heteroaryl, wherein said $C_6$-$C_{10}$ aryl group, said 5- or 6-membered monocyclic heteroaryl group and said 9- or 10-membered bicyclic heteroaryl group may be optionally substituted with $R^{17}$;

each occurrence of $R^{16}$ is independently selected from H, $C_1$-$C_{10}$ alkyl, $C_1$-$C_6$ haloalkyl, $C_1$-$C_6$ hydroxyalkyl, —($C_1$-$C_3$ alkylene)m-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and -($C_1$-$C_3$ alkylene)$_m$-(9- or 10-membered bicyclic heteroaryl), wherein said $C_3$-$C_7$ cycloalkyl group, said $C_6$-$C_{10}$ aryl group, said 4 to 7-membered heterocycloalkyl group, said -5- or 6-membered monocyclic heteroaryl group or said 9- or 10-membered bicyclic heteroaryl group may be optionally substituted with $R^{17}$;

$R^{17}$ represents from one to five substituent groups, each independently selected from $C_1$-$C_6$ alkyl, halo, —O$R^{19}$, -S$R^{19}$, $C_1$-$C_6$ haloalkyl, $C_1$-$C_6$ hydroxyalkyl, —O—($C_1$-$C_6$ haloalkyl), —CN, —NO$_2$, —N($R^{19}$)$_2$, —C(O)0$R^{19}$, —C(O)N($R^{19}$)2 and —NHC(O)$R^{19}$;

each occurence of $R^{18}$ is independently selected from H, $C_1$-$C_6$ alkyl, $C_6$-$C_{10}$ aryl, —($C_1$-$C_6$ alkylene)-O—($C_1$-$C_{20}$ alkyl), —($C_1$-$C_6$ alkylene)-O—C(O)—$R^{16}$, and —($C_1$-$C_6$ alkylene)-O—C(O)—O—$R^{16}$;

each occurrence of $R^{19}$ is independently selected from H, $C_1$-$C_{10}$ alkyl, $C_1$-$C_6$ haloalkyl, $C_1$-$C_6$ hydroxyalkyl, —($C_1$-$C_3$ alkylene)$_m$-($C_3$-$C_7$ cycloalkyl), —($C_1$-$C_3$ alkylene)$_m$-($C_6$-$C_{10}$ aryl), —($C_1$-$C_3$ alkylene)$_m$-(4 to 7-membered heterocycloalkyl), —($C_1$-$C_3$ alkylene)$_m$-(5- or 6-membered monocyclic heteroaryl) and —($C_1$-$C_3$ alkylene)$_m$-(9- or 10-membered bicyclic heteroaryl);

each occurence of $R^{20}$ is independently selected from H, $C_1$-$C_6$ alkyl and -($C_1$-$C_6$ alkylene)$_m$-Z—($C_1$-$C_3$ alkylene)$_m$-$R^{11}$;

each occurence of $R^{21}$ is independently selected from H and $C_1$-$C_6$ alkyl;

each occurrence of Z is independently selected from a bond, —O— or —N($R^9$)—;

each occurrence of m is independently 0 or 1; and n is 1 or 2.

2. The compound of claim 1, wherein A is 5 or 6-membered monocyclic heteroaryl, or a pharmaceutically acceptable salt thereof.

3. The compound of claim 1, wherein X is CH$_2$, or a pharmaceutically acceptable salt thereof.

4. The compound of claim 1, wherein Y is CH$_2$ or —CH(CH$_3$)—, or a pharmaceutically acceptable salt thereof.

5. The compound of claim 1 having the formula (Ia):

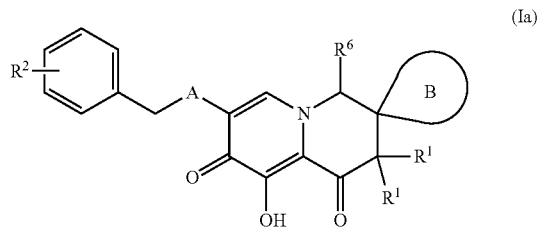

(Ia)

or a pharmaceutically acceptable salt or prodrug thereof, wherein:

A is: —NHC(O)— or:

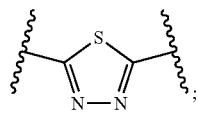

B is a 5 or 6-membered heterocycloalkyl, optionally substituted with R$^6$;

each occurrence of R$^1$ is C$_1$-C$_6$ alkyl, or both R$^1$ groups and the common carbon atom to which they are attached, join to form an exocyclic olefin group having the formula:

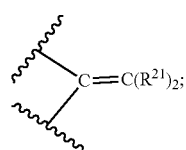

R$^2$ represents up to 3 optional substitutents, each independently selected from halo;

R$^6$ is H or C$_1$-C$_6$ alkyl; and each occurrence of R$^{21}$ is independently selected from H and C$_1$-C$_6$ alkyl.

6. The compound of claim 1, wherein A is —NHC(O)—, or a pharmaceutically acceptable salt thereof.

7. The compound of claim 1, wherein A is:

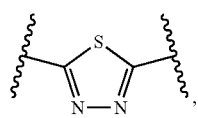

or a pharmaceutically acceptable salt thereof.

8. The compound of claim 1, wherein R$^2$ represents from 1 to 3 groups, each independently selected from F and Cl, or a pharmaceutically acceptable salt thereof.

9. The compound of claim 1, wherein B is tetrahydrofuran or tetrahydropyran, each of which can be optionally substituted with C$_1$-C$_6$ alkyl, or a pharmaceutically acceptable salt thereof.

10. The compound of claim 9, wherein B is tetrahydrofuran that is optionally substituted with methyl, or a pharmaceutically acceptable salt thereof.

11. The compound of claim 1, wherein each occurrence of R$^1$ is C$_1$-C$_6$ alkyl, or a pharmaceutically acceptable salt thereof.

12. The compound of claim 1, wherein both R$^1$ groups and the common carbon atom to which they are attached, join to form an endocyclic olefin group having the formula:

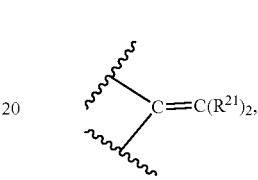

or a pharmaceutically acceptable salt thereof.

13. A compound selected from

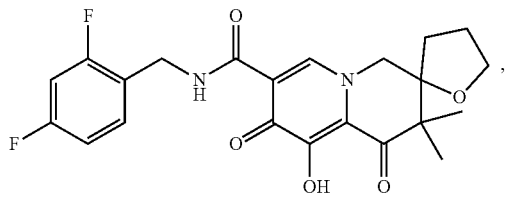

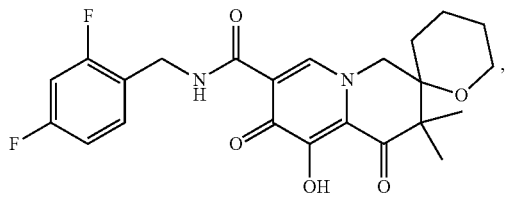

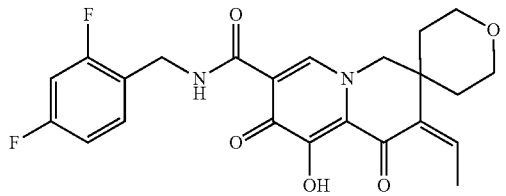

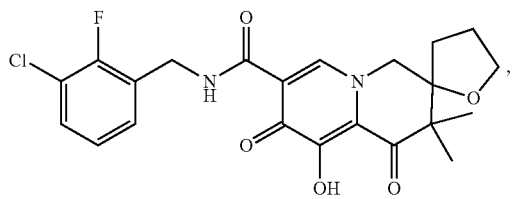

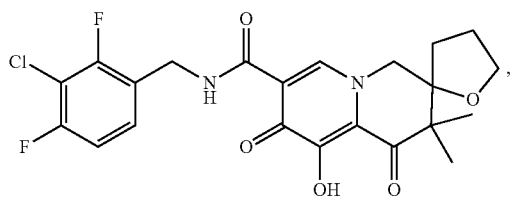

-continued

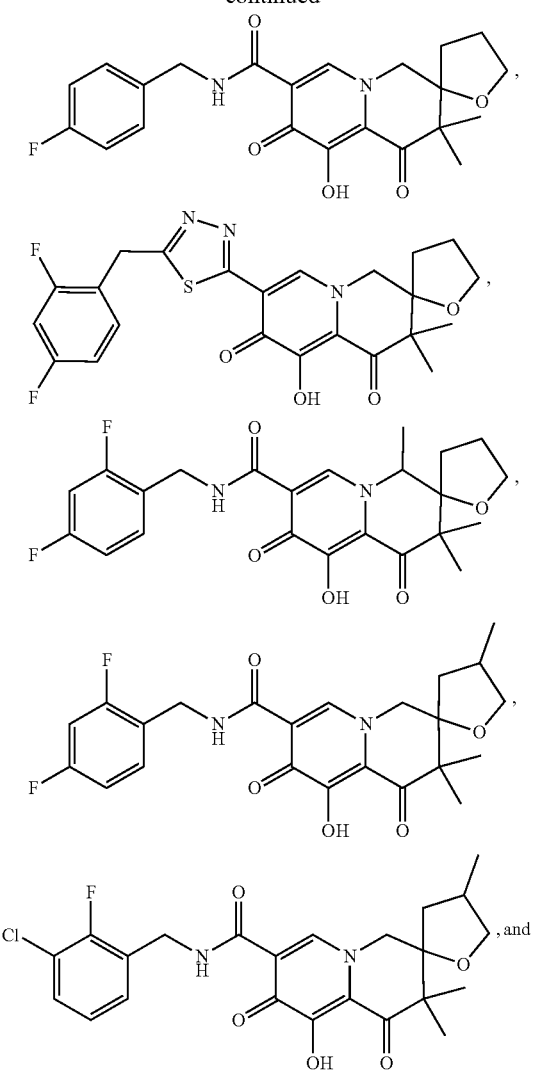

-continued

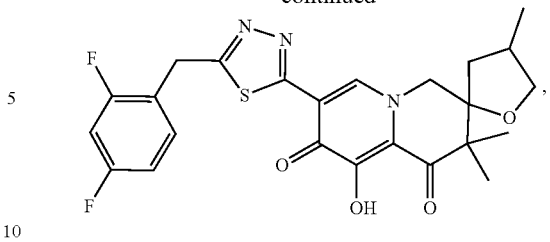

or a pharmaceutically acceptable salt thereof.

14. A pharmaceutical composition comprising an effective amount of a compound of claim 1, or a pharmaceutically acceptable salt thereof, and a pharmaceutically acceptable carrier.

15. A method for the inhibition of HIV integrase in a subject in need thereof which comprises administering to the subject an effective amount of a compound of claim 1, or a pharmaceutically acceptable salt thereof.

16. A method for the treatment of infection by HIV or for the treatment or delay in the onset or progression of AIDS in a subject in need thereof, which comprises administering to the subject an effective amount of a compound of claim 1, or a pharmaceutically acceptable salt thereof.

17. A compound of claim 1, or a pharmaceutically acceptable salt thereof, for use in the preparation of a medicament for the inhibition of HIV integrase, for the treatment of infection by HIV, or for the treatment or delay in the onset or progression of AIDS in a subject in need thereof.

18. The pharmaceutical composition of claim 14, further comprising one or more additional therapeutic agents selected from the group consisting of lamivudine, abacavir, ritonavir, darunavir, atazanavir, emtricitabine, tenofovir, rilpivirine and lopinavir.

19. The method of claim 16, further comprising administering to the subject one or more additional therapeutic agents selected from the group consisting of lamivudine, abacavir, ritonavir, darunavir, atazanavir, emtricitabine, tenofovir, rilpivirine and lopinavir, wherein the amounts administered of the compounds, are together effective to treat infection by HIV or to treat or delay the onset or progression of AIDS.

* * * * *